United States Patent
Li et al.

(10) Patent No.: US 9,458,170 B2
(45) Date of Patent: Oct. 4, 2016

(54) COMPOUND OF CAMPTOTHECIN AND PREPARATION AND USE THEREOF

(71) Applicant: Yuliang Li, Chifeng (CN)

(72) Inventors: Yuliang Li, Chifeng (CN); Huting Wang, Beijing (CN); Yan Zhu, Beijing (CN); Zhe Wang, Beijing (CN); Hui Zhang, Beijing (CN); Ruiyu Zhao, Beijing (CN); Yuanyuan Huang, Beijing (CN); He Wang, Beijing (CN); Yong Peng, Beijing (CN); Hong Luo, Beijing (CN); Dengming Xiao, Beijing (CN); Shousong Cao, Chifeng (CN); Yongxin Han, Beijing (CN)

(73) Assignee: YULIANG LI, Chifeng, Inner Mongolia (CN)

( * ) Notice: Subject to any disclaimer, the term of this patent is extended or adjusted under 35 U.S.C. 154(b) by 0 days.

(21) Appl. No.: 14/409,284

(22) PCT Filed: Jun. 17, 2013

(86) PCT No.: PCT/CN2013/077336
§ 371 (c)(1),
(2) Date: Dec. 18, 2014

(87) PCT Pub. No.: WO2013/189266
PCT Pub. Date: Dec. 27, 2013

(65) Prior Publication Data
US 2015/0166559 A1    Jun. 18, 2015

(30) Foreign Application Priority Data

Jun. 18, 2012   (CN) .......................... 2012 1 0200616
Aug. 8, 2012    (CN) .......................... 2012 1 0280442

(51) Int. Cl.
*A61K 31/4745*    (2006.01)
*C07D 491/22*    (2006.01)

(52) U.S. Cl.
CPC ................. *C07D 491/22* (2013.01)

(58) Field of Classification Search
USPC ............................................ 514/283; 546/48
See application file for complete search history.

(56) References Cited

U.S. PATENT DOCUMENTS 4,894,456 A    1/1990 Wall et al.
4,981,968 A *  1/1991 Wall .................... C07D 491/22
                                                544/361
5,106,742 A *  4/1992 Wall ...................... A61K 31/47
                                                435/183

FOREIGN PATENT DOCUMENTS

GB    2280674    2/1995
WO    9003169    4/1990
WO    9105556    5/1991

OTHER PUBLICATIONS

The Merck Manual 1288-99 (Berkow et al. eds., 17$^{th}$ ed., published in Chinese by People's Health Publishing House in 2001) (with partial English translation).
Goodman and Gilman, The Pharmacological Basis of Therapeutics 5-8 (10$^{th}$ ed. McGraw-Hill 2001).
Clinical Pharmacology 11-13 (Li ed., 4$^{th}$ ed., published by People's Medical Publishing House in 2008) (with partial English Translation).
Remington's Pharmaceutical Sciences 741-3 (14$^{th}$ ed., Mack Publishing Company 1970).
The Science and Practice of Pharmacy 777 and 801-3 (22$^{nd}$ Ed. Pharmaceutical Press 2013)
Wall et al., J. American Chemical Society, 88(16):3888-990 (1966).
Wuts and Greene, Greene's Protective Groups in Organic Synthesis 16-24, 102-19, 431-4, 448, 454-65 (4$^{th}$ ed., John Wiley & Sons, Inc. 2007).
Mu et al., Clin Pharm J, 41(11):804-6 (2006) (with partial English Translation).
Ansel et al., Drug Dosage Forms and Drug Delivery System (7$^{th}$ ed.), translated by Zhiqiang Jiang, published in Chinese by Chinese Medical Science and Technology Press in 2003, pp. 130-132 (with partial English Translation).
Carey and Sundberg, "Advanced Organic Chemistry 4th ed.," vols. A (2000) and B (2001).
Greenwald, R.B. et al., Journal of Medicinal Chemistry, 2000, vol. 43, 475-487.

(Continued)

*Primary Examiner* — Charanjit Aulakh
(74) *Attorney, Agent, or Firm* — RatnerPrestia

(57) ABSTRACT

The present disclosure relates to a compound of formula I, a pharmaceutical composition thereof and the use thereof as an anti-tumor drug.

Formula I

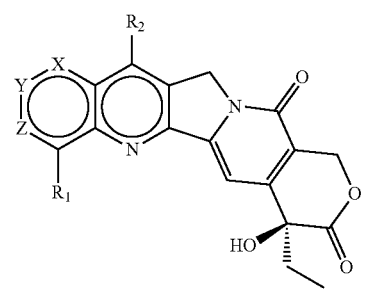

4 Claims, No Drawings

(56) References Cited

OTHER PUBLICATIONS

International Preliminary Report on Patentability and Written Opinion for International Application No. PCT/CN2013/077336 mailed Dec. 23, 2014

International Search Report for International Application No. PCT/CN2013/077336 mailed Sep. 26, 2013.

Lu, A.J., et al., Acta Pharmacol Sin, Feb. 2007, vol. 28, No. 2, pp. 307-314.

Saulnier, M.G. et al., Bioorganic & Medicinal Chemistry Letters, 1994, 4, pp. 1985-1990.

Supplementary Partial European Search Report for Application No. EP 13 80 6765 dated Nov. 2, 2015.

Terasawa et al., Heterocycles, 38(1):81 (1994).

Uehling et al., Journal of Medicinal Chemistry, 38(7):1106-18 (1995).

Wani et al, Journal of Medicinal Chemistry, American Chemical Society, US, 29(11): 2358-63 (1986).

\* cited by examiner

COMPOUND OF CAMPTOTHECIN AND PREPARATION AND USE THEREOF

CROSS-REFERENCE TO RELATED APPLICATIONS

This application is a U.S. National Stage of International Patent Application No. PCT/CN2013/077336, filed Jun. 17, 2013, which claims priority to Chinese Application Nos. 201210200616.4 filed on Jun. 18, 2012, and 201210280442.7 filed on Jun. 8, 2012, the contents of each of which are incorporated herein in their entireties for all purposes.

TECHNICAL FIELD

The disclosure relates to a series of novel camptothecin compounds with anti-tumor activities, pharmaceutical compositions and use thereof.

BACKGROUND

Camptothecin (camptothecin, CPT, IUPAC name: (S)-4-ethyl-4-hydroxy-1H-pyrano[3',4':6,7]indolizino[1,2-b]quinoline-3,14-(4H,12H)-dione) is a alkaloid compound extracted from Camptotheca acuminata (Nyssaceae, China) in 1966 firstly by Wall et al. [J. Am. Chem. Soc. 1966, 88 (16), 3888-990]. It demonstrates anti-tumor activities, particularly against leukemia and numerous solid tumors in experiments, and is a natural cytotoxic compound. By 1970s, phase I and phase II clinical trials have been carried out, and it was found that even though CPT has anti-tumor activity, it has many side effects as well. The side effects include bone marrow suppression, gastrointestinal toxicity, hemorrhagic cystitis, hair loss, diarrhea, nausea, and vomiting, etc.

In order to obtain camptothecin derivatives with high activity and low toxicity, structure modifications and optimizations have been carried out and a series of camptothecin derivatives were synthesized by semisynthesis and total synthesis methods. In 1994, FDA approved a camptothecin derivative (or named as "a camptothecin compound"), irinotecan (Irinotecan, CPT-11), for the treatment of colorectal cancer. In 1996, topotecan (Topotecan) was approved for the treatment of ovarian cancer, and further approved in 1999 by FDA as a second-line medicine for the treatment of small cell lung cancer (SCLC). Nowadays, there are more than ten camptothecin compounds in clinical trials.

Camptothecin is the second anticancer drug extracted from plants after paclitaxel. Since camptothecin compounds exhibit remarkable curative effects, broad anti-tumor spectrum, no cross resistance with other anticancer drugs, they have become one of the most widely used anti-tumor drags in clinical. However, the current camptothecin compounds still exhibit obvious side effects. Thus, improving activities and reducing toxicities of camptothecin compounds are the key targets of research.

SUMMARY

In one aspect, the present disclosure relates to a compound of formula I or a pharmaceutically acceptable salt, solvate, polymorph, tautomer or prodrug thereof:

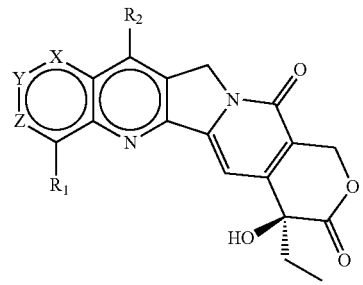

wherein:
X is $CR_3$ or N;
Y is $CR_4$ or N;
Z is $CR_5$ or N;
At least one of X, Y and Z is N;
$R_1$, $R_2$, $R_3$, $R_4$, and $R_5$ are independently selected from the group consisting of hydrogen, halogen, hydroxy, alkoxy, amino, mono (alkyl) amino, di (alkyl) amino, cycloalkyl amino, mercapto, alkylthio or cyano;
or
Both $R_3$ and $R_4$, both $R_4$ and $R_5$, or both $R_5$ and $R_1$, together with the carbon atom connecting therewith to form a 5- to 7-membered non-aromatic ring.

In another aspect, the present disclosure relates to a compound of formula I or a pharmaceutically acceptable salt, solvate, polymorph, tautomer or prodrug thereof:

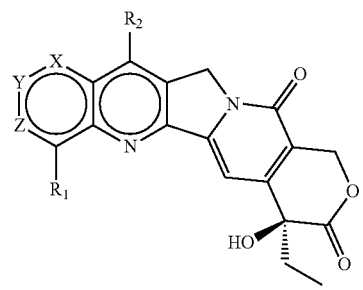

wherein:
X is $CR_3$;
Y is $CR_4$;
Z is $CR_5$;
Both $R_3$ and $R_4$, both $R_4$ and $R_5$, or both $R_5$ and $R_1$ together with their connecting carbon atoms form a 5- to 7-membered non-aromatic rings containing a heteroatom selected from the group consisting of nitrogen, oxygen or sulfur, and the other groups of $R_1$, $R_2$, $R_3$, $R_4$, $R_5$ are independently selected from the group consisting of hydrogen, halogen, hydroxy, alkoxy, amino, mono (alkyl) amino, di (alkyl) amino, cycloalkyl amino, mercapto, alkylthio or cyano; or
$R_1$, $R_2$, and $R_3$ are all hydrogen, and $R_4$ and $R_5$ are different with each other and independently selected from the group consisting of halogen, hydroxy or alkoxy; or
$R_1$ and $R_3$ are both hydrogen, $R_2$ is amino or alkyl, and $R_4$ and $R_5$ are independently selected from the group consisting of halogen, hydroxy, alkoxy, amino, mono (alkyl) amino or di (alkyl) amino.

In another aspect, the disclosure relates to a pharmaceutical composition containing the compound of the disclosure or a pharmaceutically acceptable salt, solvate, polymorph, tautomer or prodrug thereof, and a pharmaceutically acceptable carrier thereof.

In another aspect, the disclosure relates to the compound of the disclosure or a pharmaceutically acceptable salt, solvate, polymorph, tautomer or prodrug thereof, or a pharmaceutical composition thereof, which are used for the preventions and/or treatments of tumors.

In another aspect, the disclosure relates to a use of the compound of the disclosure or a pharmaceutically acceptable salt, solvate, polymorph, tautomer or prodrug thereof, or a pharmaceutical composition thereof in preparation of an anti-tumor drug.

In another aspect, the present disclosure provides a method for preventing and/or treating tumors in mammals, especially in humans, which method contains administering to a mammal, especially a human, in need thereof a therapeutically effective amount of the compound of the disclosure, or a pharmaceutically acceptable salt, solvate, polymorph, tautomer or prodrug thereof or a pharmaceutical composition thereof.

DETAILED DESCRIPTIONS

Definitions

Unless defined otherwise, all technical and scientific terms used herein have the same meanings as are commonly understood by one of skilled in the art to which the claimed subject matter belongs. All patents, patent applications, published materials referred to throughout the entire disclosure herein, unless noted otherwise, are incorporated by reference in their entirety.

It is to be understood that the foregoing general description and the following detailed description are exemplary and explanatory only and are not restrictive of any subject matter claimed. In this disclosure, the use of the singular includes the plural unless specifically stated otherwise. It must be also noted that, use of "or" means "and/or" unless stated otherwise. Furthermore, use of the term "containing" as well as other forms, such as "contain", "contains", and "contained" are not limited. Likewise, use of the term "comprising" as well as other forms, such as "comprise", "comprises", and "comprised" are not limited.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, IR and UV/Vis spectroscopy and pharmacology, within the skill of the art are employed. Unless specific definitions are provided, the nomenclature employed in connection with analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits manufacturer's specifications or as commonly accomplished in the art or as described herein. The foregoing techniques and procedures can be generally performed by conventional methods well known in the art and as described in various general and more specific references that are cited and discussed throughout the present disclosure. Throughout the specification, groups and substituents can be chosen by one skilled in the field to provide stable moieties and compounds.

Where substituent or groups are specified by their conventional chemical formulas, written from left to right, they equally encompass the chemically identical substituents that would result from writing the structure from right to left. As a non-limiting example, —CH$_2$O— is equivalent to —OCH$_2$—.

The section headings used herein are for organizational purposes only and are not to be construed as limiting the subject matter described. All documents, or portions of documents, cited in the disclosure including, without limitation, patents, patent applications, articles, books, manuals, and treatises are hereby incorporated by reference in their entirety for any purpose.

Certain chemical groups named herein may be preceded by a shorthand notation indicating the total number of carbon atoms that are to be found in the indicated chemical group. For example, C$_{1-6}$ alkyl describes an alkyl group, as defined below, having a total of 1 to 6 carbon atoms. The total number of carbons in the shorthand notation does not include carbons that may exist in substituents of the group described.

In addition to the foregoing, as used in the specification and appended claims, unless specified to the contrary, the following terms have the meaning indicated below.

In the present disclosure, term "halo" or "halogen" refers to bromo, chloro, fluoro or iodo.

"Hydroxy" refers to —OH.
"Mercapto" refers to —SH.
"Oxo" refers to =O.
"Cyano" refers to —CN.
"Amino" refers to —NH$_2$.

In the present disclosure, as used alone or as a part of another moiety (such as in halogen-substituted alkyl and the like), the term "alkyl" refers to a straight or branched mono-valent hydrocarbon chain radical consisting solely of carbon and hydrogen atoms, containing no unsaturation, having from one to twelve carbon atoms, preferably one to eight carbon atoms and more preferably one to six carbon atoms, and which is attached to the rest of the molecule by a single bond. Examples of the alkyls include, but not limited to, methyl, ethyl, n-propyl, iso-propyl, n-butyl, iso-butyl, sec-butyl, tert-butyl, n-pentyl, 2-methylbutyl, 2,2-dimethylpropyl, n-hexyl, heptyl, 2-methylhexyl,3-methylhexyl, octyl, nonyl, decyl, and the like.

As used herein, the term "alkoxy" refers to a radical of the formula —OR$_a$ where R$_a$ is an alkyl radical as defined above. Examples of the alkoxy radical include, but not limited to, methoxy, ethoxy, propoxy, iso-propoxy, n-butoxy, iso-butoxy, sec-butoxy, tert-butoxy, and the like.

As used herein, the term "alkylsulfanyl" refers to a radical of the formula —SR$_a$ where R$_a$ is an alkyl radical as defined above. Examples of the alkylsulfanyl radical include, but not limited to, methylsulfanyl, ethylsulfanyl, propylsulfanyl, iso-propylsulfanyl, and the like.

As used herein, the term "mono(alkyl)amino" refers to a radical of the formula —NHR$_s$ where R$_a$ is an alkyl radical as defined above. Examples of the mono(alkyl)amino radical include, but not limited to, methylamino, ethylamino, iso-propylamino, and the like.

As used herein, the term "di(alkyl)amino" refers to a radical of the formula —NR$_a$R$_b$ where R$_a$ and R$_b$ are each independently an alkyl radical as defined above. Examples of the dialkylamino radical include, but not limited to, dimethyl amino, diethylamino, dipropylamino, methylethylamino, and the like.

As used alone or as a part of another moiety, the term "cycloalkyl" refers to a stable mono-valent non-aromatic monocyclic or polycyclic hydrocarbon radical consisting solely of carbon and hydrogen atoms, which may include fused, bridged, or spiro ring systems, having from three to fifteen carbon atoms, preferably having from three to ten carbon atoms, more preferably having from three to eight carbon atoms, and which is saturated or unsaturated and attached to the rest of a molecule by a single bond. Unless stated otherwise in the specification, the carbon atoms of the cycloalkyl can be optionally oxidized. Examples of cycloalkyl include, but not limited to, cyclopropyl, cyclobutyl, cyclopentyl, cyclopentenyl, cyclohexyl, cyclohexenyl, cyclohexdienyl, cycloheptyl, cyclooctyl, 1H-indenyl, 2,3-dihydro-indenyl, 1,2,3,4-tetrahydro-naphthyl, 5,6,7,8-tetrahydro-naphthyl, 8,9-dihydro-7H-benzocyclohepten-6-yl, 6,7,8,9-tetrahydro-5H-benzocycloheptenyl, 5,6,7,8,9,10-hexahydro-benzocyclooctenyl, fluorenyl, dicyclo[2.2.1]heptyl, 7,7-dimethyl-dicyclo[2.2.1]heptyl, dicyclo[2.2.1]heptenyl, dicyclo[2.2.2]octyl, dicyclo[3.1.1]heptyl, dicyclo[3.2.1]octyl, dicyclo[2.2.2]octenyl, dicyclo[3.2.1]octenyl, adamantyl, octahydro-4,7-methylene-1H-indenyl, octahydro-2,5-methylene-pentalinyl, and the like.

As used herein, the term "cycloalkylamino" refers to a radical of the formula —$NHR_c$ where $R_c$ is a cycloalkyl radical as defined above.

As used alone or as a part of another moiety, the term "heterocyclyl" refers to a stable 3- to 20-membered mono-valent non-aromatic ring radical which consists of two to fourteen carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or polycyclic ring system, which may include fused, bridged, or spiro ring systems; and the nitrogen, carbon or sulfur atoms in the heterocyclyl radical may be optionally oxidized; the nitrogen atom may be optionally quaternized; and the heterocyclyl radical may be partially or fully saturated. A heterocyclyl may be connected to the rest of a molecule by a single bond via a carbon atom or a heteroatom on the ring. In a heterocyclyl containing a fused ring, one or more of the rings may be an aryl or heteroaryl, provided that the site for connecting to the rest of the molecule is a non-aromatic ring atom. In the present disclosure, the heterocyclyl is preferably a stable 4- to 11-membered mono-valent non-aromatic mono-cyclic, di-cyclic, bridged or spiro ring radical which comprises one to three heteroatoms selected from the group consisting of nitrogen, oxygen and sulfur, and more preferably a stable 5- to 7-membered non-aromatic mono-cyclic ring radical which comprises one heteroatom selected from the group consisting of nitrogen, oxygen and sulfur. Examples of heterocyclyl radicals include, but are not limited to, pyrrolidinyl, morpholinyl, piperazine, homopiperazine, piperidyl, thiomorpholinyl, 2,7-diaza-spiro[3.5]nonane-7-yl, 2-oxa-6-aza-spiro[3.3]heptane-6-yl, 2,5-diaza-bicyclo[2.2.1]heptane-2-yl, azacyclobutyl, pyranyl, tetrahydropyranyl, thiopyranyl, tetrahydrofuranyl, oxazinl, dioxocyclopentyl, tetrahydroisoquinolinyl, decahydroisoquinolinyl, imidazolinyl, imidazolidinyl, quinolizinyl, thiazolidinyl, isothiazolidinyl, isoxazolidinyl, dihydroindolyl, octahydroindolyl, octahydroisoindolyl, pyrrolidinyl, pyrazolidinyl, phthalimido, and the like.

The term "fused" as used herein, alone or in combination, refers to cyclic structures in which two or more rings share one or more bonds.

As used herein, the term "non-aromatic ring" includes the cycloalkyl and heterocyclyl defined above. The non-aromatic ring herein can include unsaturated bonds, while not result in the generation of aromaticity.

The term "aromatic" as used herein, refers to a cyclic or polycyclic, ring moiety having a delocalized at-electron system containing 4n+2 electrons, where n is an integer.

"Optional" or "optionally" as used herein means that the subsequently described event or circumstances may or may not occur, and that the description includes instances where said event or circumstance occurs and instances in which it does not. For example, "optionally substituted alkyl" means that the alkyl radical may or may not be substituted and that the description includes both substituted alkyl radicals and alkyl radicals having no substitution.

The terms "moiety", "structure moiety", "chemical moiety", "group", "substituent" and "chemical Group", as used herein, refer to a specific segment or functional group of a molecule. Chemical moieties are often recognized chemical entities embedded in or appended to a molecule.

As the compounds described herein contain olefinic double bonds, unless specified otherwise, it is intended that the compounds include both E and Z geometric isomers.

A "tautomer" refers to an isomer resulted from a proton shift from one atom of a molecule to another atom of the same molecule. The present disclosure includes tautomers of any said compounds.

As used herein, the term "pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids or organic acids. Inorganic acid salts include, but are not limited to, hydrochlorate, hydrobromate, sulfate, nitrate, phosphate and the like, and organic acid salts include, but not limited to, formate, acetate, 2,2-dichloroacetate, trifluoride acetate, propionate, caproate, octanoate, decanoate, undecylenate, glycollate, gluconate, lactate, sebacate, adipate, glutarate, malonate, oxalate, maleate, succinate, fumarate, tartrate, citrate, palmitate, stearate, oleate, cinnamate, laurate, malate, glutamate, pyroglutamate, aspartate, benzoate, mesylate, benzene sulfonate, p-toluenesulfonate, alginate, ascorbate, salicylate, 4-amino salicylate, napadisilate, and the like. The salts can be prepared by conventional methods in this art.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethyamine, tripropylamine, ethanolamine, diethanolamine, triethanolamine, deanol, 2-dimethylaminoethanol, 2-diethylaminoethanol, dicyclohexylamine, lysine, arginine, histidine, caffeine, procaine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine. These salts can be prepared by the methods well known in the art.

The term "polymorph" or "polymorphism" as used herein refers to compounds of this disclosure present in different crystal lattice forms, which were resulted from two or more than two different molecular arrangement. Some of the compounds of the present disclosure may have more than one crystal form, and the present disclosure tends to encompass all the polymorphs or mixtures thereof.

Crystallizations often produce a solvate of the compound of the disclosure. As used herein, the term "solvate" refers to an aggregate that comprises one or more molecules of a compound of the disclosure with one or more molecules of solvent. The solvent may be water, in which case the solvate is a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the disclosure may be true solvates, while in other cases, the compound of the disclosure may merely retain adventitious water or a mixture of water plus some adventitious solvent. The compounds of the present disclosure may react in a solvent or deposit or crystallize from a solvent. The solvates of the compounds of the present disclosure are also encompassed in the scope of the present disclosure.

The present disclosure also includes a prodrug of the compounds of the present disclosure, "A prodrug" is meant to indicate a compound that may be converted under physiological conditions or by solvolysis to a biologically active compound of the disclosure. Thus, the term "prodrug" refers to a metabolic precursor of a compound of the disclosure that is pharmaceutically acceptable. A prodrug may be inactive when administered to a subject in need thereof, but is converted in vivo to an active compound of the disclosure. A prodrug is typically rapidly transformed in vivo to yield the parent compound of the disclosure, for example, by hydrolysis in blood. The prodrug compound often offers advantages of solubility, tissue compatibility or delayed release in a mammalian organism. A prodrug includes amino protective groups and carboxy protective groups which are known to persons skilled in the art. Methods for preparing specific prodrugs are provided in e.g. Saulnier, M. G., et al., *Bioorg. Med. Chem. Lett.* 1994, 4, 1985-1990; Greenwald, R. B., et al., *J. Med. Chem.* 2000, 43, 475.

As used herein, "pharmaceutical composition" refers to a formulation of the compound of this disclosure and a medium generally accepted in the art for the delivery of the biologically active compound to mammals, e.g., human beings. Such a medium includes all pharmaceutically acceptable carriers thereof. The purposes of a pharmaceutical composition are promoting administration of organisms, facilitating the absorption of active ingredients and exerting its biological activity.

The term "pharmaceutically acceptable" as used herein, refers to a material, such as a carrier or diluent, which does not influence the biological activity or properties of the compounds described herein, and is relatively nontoxic, i.e., the material may be administered to an individual without causing undesirable biological effects or interacting in a deleterious manner with any of the components of the composition in which it is contained.

"Pharmaceutically acceptable carrier" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by relevant government administration as being acceptable for use in humans or domestic animals.

The term "subject", "patient" or "individual" as used herein in reference to individuals suffering from a disease, a disorder, a condition, and the like, encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human being.

The terms "prevention of", "prophylaxis", "prevent" or "preventing" includes reducing the likelihood of a patient incurring or developing a disease or condition.

As used herein, term "treating" or other similar synonyms includes meanings as below;
 (i) preventing the disease or condition from occurring in a mammal, in particular, when such mammal is predisposed to the condition but has not yet been diagnosed as having it;
 (ii) inhibiting the disease or condition, i.e., arresting its development;
 (in) relieving the disease or condition, i.e., causing regression of the disease or condition; or
 (iv) relieving the symptoms resulting from the disease or condition.

The terms "effective amount", "therapeutically effective amount" or "pharmaceutically effective Amount" as used herein, refer to a sufficient amount of at least one agent or compound being administered which will relieve to some extent one or more of the symptoms of the disease or condition, being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer", "administering", "administration", and the like, as used herein, refer to the methods that may be used to enable deliver of the compound or composition to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Oilman, The Pharmacological Basis of Therapeutics, current ed.; Pergamon; and Remington's, *Pharmaceutical Sciences* (current edition), Mack Publishing Co., Easton, Pa. In some preferred embodiments, the compounds and compositions described herein are administered orally.

The terms "pharmaceutical combination", "pharmaceutical co-administration", "administered in Combination" "administering an additional therapy", "administering an additional therapeutic agent" and the like, as used herein, refer to a pharmaceutical therapy resulting from mixing or combining more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

EMBODIMENTS

In one aspect, the present disclosure relates to a compound of formula I or a pharmaceutically acceptable salt, solvate, polymorph, tautomer or prodrug thereof:

Formula I

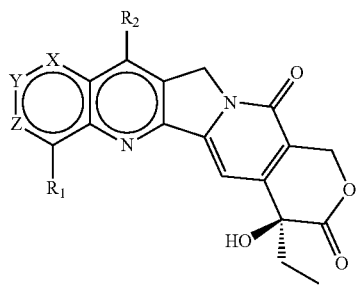

wherein:

X is $CR_3$ or N;

Y is $CR_4$ or N;

Z is $CR_5$ or N;

At least one of X, Y and Z is N;

$R_1$, $R_2$, $R_3$, $R_4$ and $R_5$ are independently selected from the group consisting of hydrogen, halogen, hydroxy, alkoxy, amino, mono (alkyl) amino, di (alkyl) amino, cycloalkyl amino, mercapto, alkylthio or cyano;

or both $R_3$ and $R_4$, both $R_4$ and $R_5$, or both $R_5$ and $R_1$, together with the carbon atoms to which they link form a 5- to 7-membered non-aromatic rings.

In a preferred embodiment, the present disclosure relates to a compound of formula I or a pharmaceutically acceptable salt, solvate, polymorph, tautomer or prodrug thereof, wherein:

$R_1$, $R_2$, $R_3$, $R_4$ and $R_5$ are independently selected from the group consisting of hydrogen, halogen, hydroxy, $C_{1-6}$ alkoxy, amino, mono ($C_{1-6}$ alkyl) amino, di ($C_{1-6}$ alkyl) amino, $C_{3-8}$ cycloalkyl amino, mercapto, $C_{1-6}$ alkylthio or cyano;

or both $R_3$ and $R_4$, both $R_4$ and $R_5$, or both $R_5$ and $R_1$, together with the carbon atoms to which they link form a 5- to 7-membered non-aromatic rings having zero to three heteroatoms selected from the group consisting of nitrogen, oxygen, or sulfur.

In a more preferable embodiment, the present disclosure relates to a compound of formula I or a pharmaceutically acceptable salt, solvate, polymorph, tautomer or prodrug thereof, wherein:

$R_1$, $R_2$, $R_3$, $R_4$ and $R_5$ are independently selected from the group consisting of hydrogen, hydroxy, $C_{1-6}$ alkoxy, amino, mono ($C_{1-6}$ alkyl) amino, di ($C_{1-6}$ alkyl) amino, mercapto, or $C_{1-6}$ alkylthio;

In a more preferable embodiment, the present disclosure relates to a compound of formula I or a pharmaceutically acceptable salt, solvate, polymorph, tautomer or prodrug thereof, wherein:

$R_1$ and $R_2$ are both hydrogen; and $R_3$, $R_4$, and $R_5$ are independently selected from the group consisting of hydrogen, hydroxy, $C_{1-6}$ alkoxy, amino, mono ($C_{1-6}$ alkyl) amino, or di ($C_{1-6}$ alkyl) amino.

In a more preferable embodiment, the present disclosure relates to a compound of formula I or a pharmaceutically acceptable salt, solvate, polymorph, tautomer or prodrug thereof, wherein the compound is selected from the group consisting of:

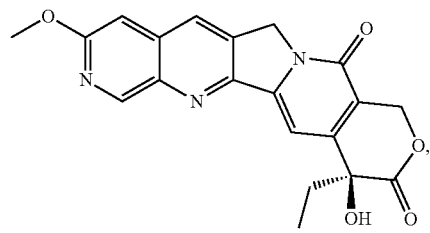

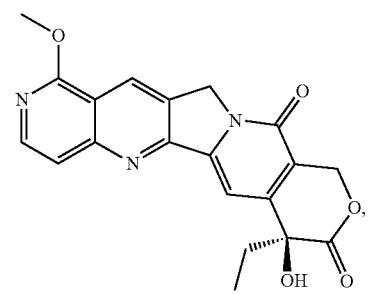

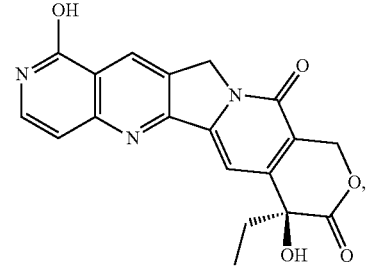

-continued

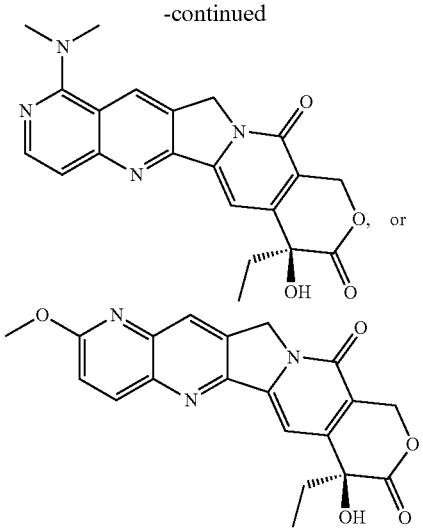

In another aspect, the present disclosure relates to a compound of formula I or a pharmaceutically acceptable salt, solvate, polymorph, tautomer or prodrug thereof:

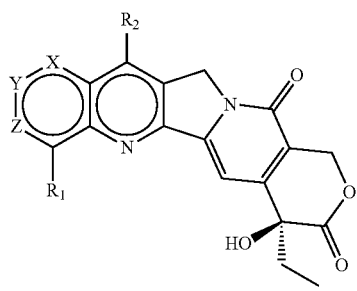

I wherein:
X is $CR_3$;
Y is $CR_4$;
Z is $CR_5$;
both $R_3$ and $R_4$, both $R_4$ and $R_5$, or both $R_5$ and $R_1$ together with the carbon atoms they link to form a 5- to 7-membered non-aromatic ring having one heteroatom selected from the group consisting of nitrogen, oxygen, or sulfur, and the rest radicals of $R_1$, $R_2$, $R_3$, $R_4$ and $R_5$ are independently selected from the group consisting of hydrogen, halogen, hydroxy, alkoxy, amino, mono (alkyl) amino, di (alkyl) amino, cycloalkyl amino, mercapto, alkylthio or cyano; or $R_1$, $R_2$, and $R_3$ are all hydrogen, and $R_4$ and $R_5$ are different and independently selected from the group consisting of halogen, hydroxy, or alkoxy; or $R_1$, $R_3$ are both hydrogen, and $R_2$ is amino or alkyl, and $R_4$ and $R_5$ are independently selected from the group consisting of halogen, hydroxy, alkoxy, amino, mono (alkyl) amino, or di (alkyl) amino.

In a preferred embodiment, the present disclosure relates to a compound of formula I or a pharmaceutically acceptable salt, solvate, polymorph, tautomer or prodrug thereof, wherein:
both $R_4$ and $R_5$ together with the carbon atoms they link to form a 5- to 7-membered non-aromatic ring having one heteroatom selected from the group consisting of nitrogen, oxygen, or sulfur, and $R_1$, $R_2$ and $R_3$ are independently selected from the group consisting of hydrogen, halogen, hydroxy, $C_{1-6}$ alkoxy, amino, mono ($C_{1-6}$ alkyl) amino, di ($C_{1-6}$ alkyl) amino, or $C_{3-8}$ cycloalkylamino.

In a more preferable embodiment, the present disclosure relates to a compound of formula I or a pharmaceutically acceptable salt, solvate, polymorph, tautomer or prodrug thereof, wherein:
both $R_4$ and $R_5$ together with the carbon atoms they link to form a 5-membered non-aromatic ring having one heteroatom selected from the group consisting of nitrogen, oxygen, or sulfur, and $R_1$, $R_2$, and $R_3$ are all hydrogens.

In a another preferred embodiment, the present disclosure relates to a compound of formula I or a pharmaceutically acceptable salt, solvate, polymorph, tautomer or prodrug thereof, wherein:
$R_1$, $R_2$ and $R_3$ are all hydrogens, and $R_4$ and $R_5$ are different and independently selected from the group consisting of halogen, hydroxy, or $C_{1-6}$ alkoxy.

In a another preferred embodiment, the present disclosure relates to a compound of formula I or a pharmaceutically acceptable salt, solvate, polymorph, tautomer or prodrug thereof, wherein:
$R_1$ and $R_3$ are both hydrogens, and $R_2$ is amino or $C_{1-6}$ alkyl, and $R_4$ and $R_5$ are independently selected from the group consisting of halogen, hydroxy, or $C_{1-6}$ alkoxy.

In a more preferable embodiment, the present disclosure relates to a compound of formula I or a pharmaceutically acceptable salt, solvate, polymorph, tautomer or prodrug thereof, wherein the compound is selected from the group consisting of:

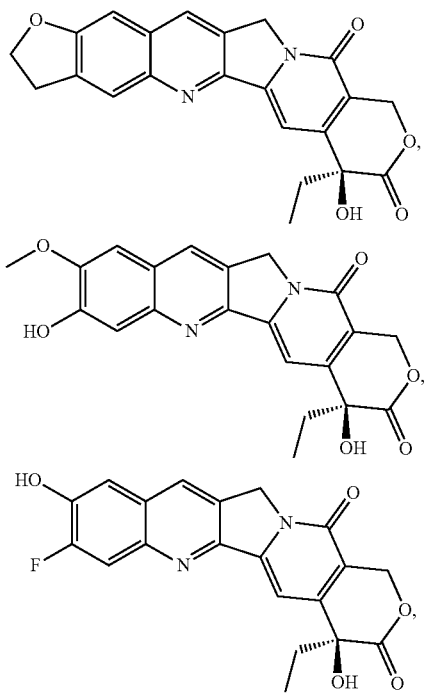

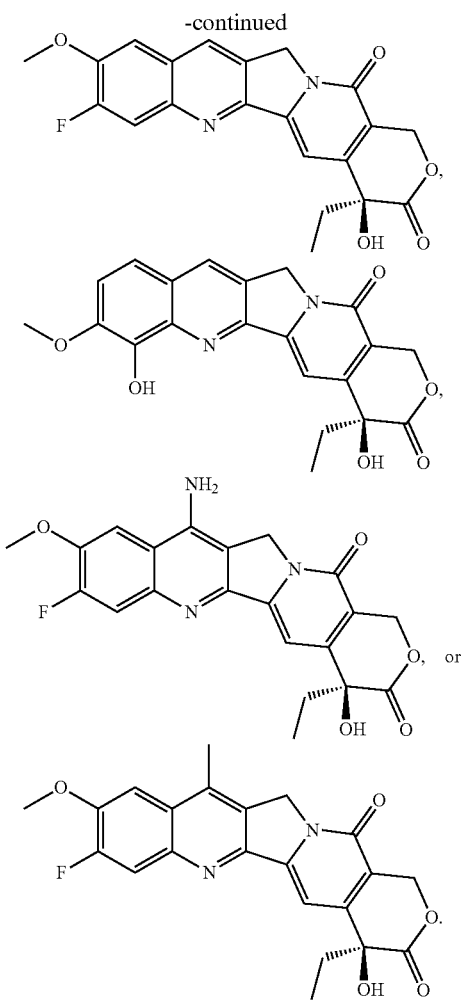

In another aspect, the present disclosure provides a pharmaceutical composition which comprises a compound of the disclosure, or a pharmaceutically acceptable salt, solvate, polymorph, tautomer or prodrug thereof, as well as a pharmaceutically acceptable carrier.

The pharmaceutical composition of the disclosure may be formulated into preparations in solid, semi-solid, liquid or gaseous forms, such as tablets, capsules, powders, granules, ointments, solutions, suppositories, injections, inhalants, gels, microspheres, and aerosols.

The pharmaceutical composition of the disclosure may be prepared by methodology well known in the pharmaceutical art. For example, a pharmaceutical composition intended to be administered by injection can be prepared by combining a compound of the disclosure with sterile distilled water so as to form a solution. A surfactant may be added to facilitate the formation of a homogeneous solution or suspension. The methods of preparing such dosage forms are known to those skilled in this art, for example, see The Science and Practice of Pharmacy, 20th Edition (Philadelphia College of Pharmacy and Science, 2000).

Typical routes of administering the pharmaceutical compositions include, without limitation, oral, topical, transdermal, intramuscular, intravenous, inhalation, parenteral, sublingual, rectal, vaginal, and intranasal. For example, dosage forms suitable for oral administration include capsules, tablets, granules, and syrups. The dosage forms may be solid powders or granules; solutions or suspensions in aqueous or non-aqueous liquids; emulsions of oil-in-water type of water-in-oil type; and the like. The above mentioned dosage forms may be prepared from active compounds and one or more carriers or auxiliaries through common pharmaceutical methods. The carriers shall be compatible with the active compounds or the other auxiliaries. For solid formulations, commonly used non-toxic carriers include, but are not limited to, mannitol, lactose, starch, magnesium stearate, cellulose, glucose, sucrose, and the like. Carriers for liquid formulations include, but are not limited to, water, physiological saline, aqueous solution of glucose, ethylene glycol, polyethylene glycol, and the like. The active compound may form a solution or a suspension with the above carriers. The specific route of administration and dosage form depend on the physical/chemical properties of the compound per se and the severity of the disease to be treated, and can be routinely determined by a person skilled in the art. For example, see Li Jun, "Clinical Pharmacology", People's Medical Publishing House, 2008.06; Ding Yufeng, "Discussion on Clinical Dosage Form Factors and Drug Rational Use in Hospital", Herald of Medicine, 26 (5), 2007; wrote by Howard C. Ansel, Loyd V. Allen, Jr., Nicholas G. Popovich, master translator Jiang Zhiqiang, "Drug Dosage Forms and Drug Delivery System", Chinese Medical Science and Technology Press, 2003.05.

In another aspect, the disclosure relates to a compound of the disclosure or a pharmaceutically acceptable salt, solvate, polymorph, tautomer or prodrug thereof, or a pharmaceutical composition thereof, which is used for the prevention and/or treatment of tumors.

In another aspect, the disclosure relates to use of a compound of the disclosure or a pharmaceutically acceptable salt, solvate, polymorph, tautomer or prodrug thereof, or a pharmaceutical composition thereof in the preparations of an anti-tumor drug.

In another aspect, the present disclosure provides a method for preventing and/or treating tumors in mammals, especially in human beings, which method comprises administering to a mammal, especially a human being in need thereof a therapeutically effective amount of a compound of the disclosure, or a pharmaceutically acceptable salt, solvate, polymorph, tautomer or prodrug thereof or a pharmaceutical composition thereof.

The term "tumor(s)" used herein includes, but is not limited to, leukemia, gastrointestinal stromal tumor, tissue cell lymphoma, non-small cell lung cancer, small cell lung cancer, pancreatic cancer, lung cancer, lung squamous carcinoma, adenocarcinoma of the lung, breast cancer, prostate cancer, liver cancer, skin cancer, cell carcinoma, cervical cancer, ovarian cancer, intestinal cancer, colon cancer, nasopharyngeal cancer, brain cancer, bone cancer, esophageal cancer, melanoma, renal cancer, oral cancer and other diseases.

Generally, a therapeutically effective daily dose is from about 0.001 mg/Kg body weight to about 100 mg/Kg body weight; preferably a therapeutically effective dose is from about 0.01 mg/Kg body weight to about 50 mg/Kg body weight; more preferably a therapeutically effective dose is from about 1 mg/Kg body weight to about 25 mg/Kg body weight.

The ranges of effective doses provided herein are not intended to be limiting and represent preferred dose ranges. However, the most preferred dosage will be tailored to the individual subject, as is understood and determinable by one skilled in the relevant arts (see, e.g., Berkow et al., eds., The Merck Manual, 16th edition, Merck and Co., Rahway, N.J., 1992).

The compound of the present disclosure can be united in or combined with one or more other compounds herein or one or more other anti-tumor drags together to treat and/or prevent tumors. The drugs which can be combined with the compound of the present disclosure include, but are not limited to, docetaxel, gemcitabine, cisplatin, carbopiatin, gleevec, temozolomide, adriamycin, dacarbazine, tarceva, etoposide, daunorubicin, cytarabine, and the like.

Experimental Section

The following Reaction Schemes illustrate methods of preparing the compounds of this disclosure.

It is understood by those skilled in the art that in the following description, combinations of various substituents of the depicted formulae are permissible only if such combinations result in stable compounds.

It will also be appreciated by those skilled in the art that in the process described below the functional groups of intermediate compounds may need to be protected by suitable protecting groups. Such functional groups include hydroxyl, amino, mercapto and carboxyl. Suitable protecting groups for hydroxyl include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxyl include alkyl, aryl or arylalkyl esters.

Protecting groups may be added or removed in accordance with standard techniques, which are known to one skilled in the art and are as described herein.

The use of protecting groups is described in detail in Greene, T. W. and P. G. M. Wuts, *Greene's Protective Groups in Organic Synthesis* (1999), 4th Ed., Wiley. The protecting group may also be polymer resin.

The compound of formula I of the present disclosure may be prepared following the procedures illustrated in Scheme 1 or Scheme 2.

Scheme 1:

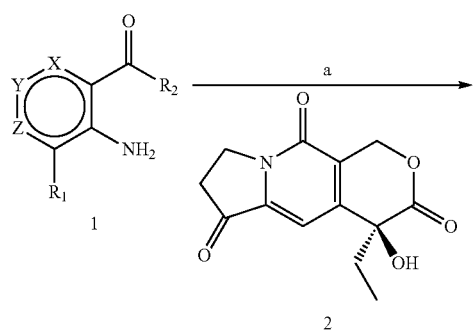

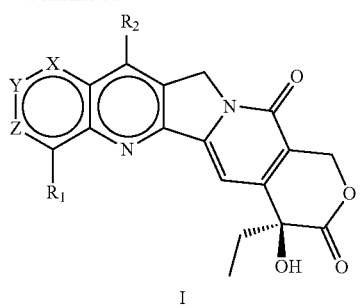

Experimental condition: a. p-toluenesulfonic acid (cat.), methylbenzene, reflux.

Scheme 2:

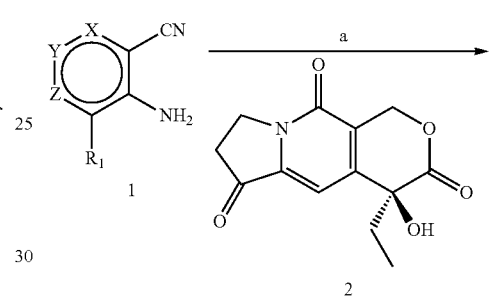

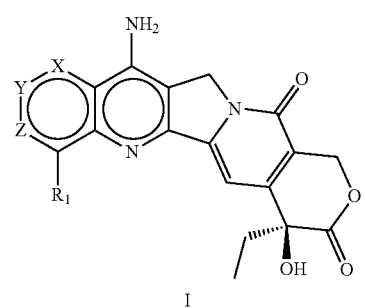

Experimental condition: a. p-toluenesulfonic acid (cat.), methylbenzene, reflux.

Compound 2 used in Scheme 1 and 2 can be prepared following the procedures as below.

(S)-4-ethyl-4-hydroxy-7,8-dihydro-1H-pyrano[3,4-f]indolizine-3,6,10(4H)-trione

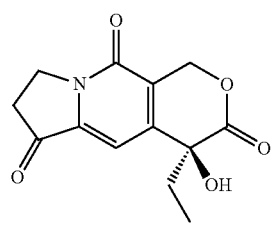 [SMILES: CC[C@@]1(O)C(=O)OCc2c1cc1n(c2=O)CCC1=O]

Step 1: ethyl 2,4-dioxo-valerate

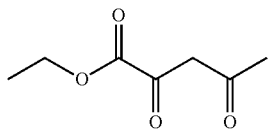

Na (25.3 g, 1.1 mol) was added to anhydrous EtOH (600 mL) within 30 min, and the mixture was stirred at room temperature for 2 h. Then, a mixture of diethyl oxalate (146 g, 1.0 mol) and dry acetone (58 g, 1.0 mol) was added slowly dropwise within 3 h. The reaction mixture was stirred at room temperature for additional 1 h, and then was filtered. The obtained filter cake was added into a mixture of ice (500 g) and water (1 L), and then concentrated sulfuric acid was added to adjust the pH to 1, extracted with EtOAc. The EtOAc layer was washed with brine, dried over anhydrous sodium sulfate, and concentrated under vacuum to give the title compound (95 g, 60%). $^1$H NMR (CDCl$_3$): δ 6.37 (1H, s), 4.35 (2H, q, J=7.2 Hz), 2.26 (3H, s), 1.38 (3H, t, J=7.2 Hz).

Step 2: methyl 6-cyano-1-hydroxy-7-methyl-5-oxo-3,5-dihydroindolizine-2-carboxylate

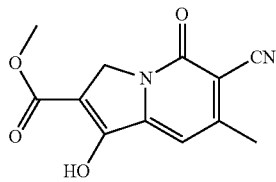 [SMILES: COC(=O)C1=C(O)c2cc(C)c(C#N)c(=O)n2C1]

A mixture of 2,4-dioxo-ethyl valerate (95 g, 0.60 mol), triethyl orthoformate (177.6 g, 1.2 mol), p-toluene sulfonic acid monohydrate (2.28 g, 12 mmol) and anhydrous methanol (150 mL) was stirred at 40° C. for 1 h, then cyano acetamide (55.0 g, 0.66 mol), potassium carbonate (91 g, 0.66 mol) and dimethyl sulfoxide (2 L) were added. The reaction mixture was heated to 70° C., and stirred for 3 h. Then, methyl acrylate (413 g, 4.8 mol) was added dropwise within 2 h, and stirred overnight at 70° C. The reaction mixture was cooled to room temperature, poured into water (30 L), added concentrated sulfuric acid to regulate pH=1, and stirred for additional 1 h at room temperature. The mixture was filtered, and the filter cake was washed with methanol and dried to obtain the title compound (45.5 g, 31%). $^1$H NMR (DMSO-d$_6$): δ 6.79 (1H, s), 4.62 (2H, s), 3.73 (3H, s), 2.43 (3H, s).

Step 3: 7-methyl-1,5-dioxo-1,2,3,5-tetrahydroindolizine-6-carbonitrile

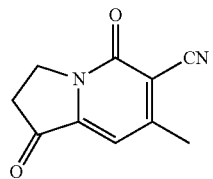

Methyl 6-cyano-1-hydroxy-7-methyl-5-oxo-3,5-dihydroindolizine-2-carboxylate (45.5 g, 185 mmol) was added to a mixture of concentrated hydrochloric acid and acetic acid (1:1), and heated to 100° C., and then stirred for 2 h, and cooled to the room temperature. The reaction mixture was concentrated under vacuum to give the title compound (34.0 g, 97.8%), $^1$H NMR (DMSO-d$_6$): δ 6.84 (1H, s), 4.08 (2H, t, J=6.4 Hz), 2.85 (2H, t, J=6.4 Hz), 2.46 (3H, s).

Step 4: 7'-methyl-5'-oxo-3',5'-dihydro-2'H-spiro[[1,3]dioxolane-2,1'-indolizine]-6'-carbonitrile

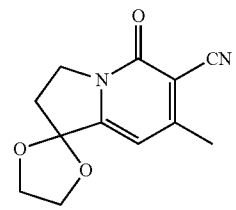 [SMILES: Cc1cc2n(c(=O)c1C#N)CCC21OCCO1]

7-Methyl-1,5-dioxo-1,2,3,5-tetrahydroindolizine-6-carbonitrile (34.0 g, 181 mmol) was dissolved in dichloromethane (1.5 L), and glycol (22.4 g, 361 mmol) and chlorotrimethylsilane (78.1 g, 723 mmol) were added. The mixture was stirred at 25° C. for 72 h under N$_2$. The reaction mixture was filtered to remove the black float, and then washed with 1 M sodium hydroxide solution. The organic layer was washed with brine, dried over anhydrous sodium sulfate, and concentrated under vacuum. The resulting residue was purified by column chromatography to give the title compound (32.0 g, 76%). $^1$H NMR (CDCl$_3$): δ 6.19 (1H, s), 4.19-4.11 (6H, m), 2.48 (3H, s), 2.39 (2H, t, J=7.8 Hz).

Step 5: ethyl 2-(6'-cyan-5'-oxo-3',5'-dihydro-2'H-spiro[[1,3]dioxolane-2,1'-indolizine]-7'-yl)acetate

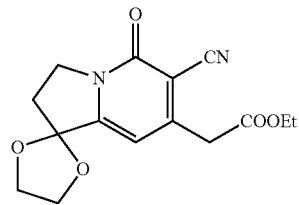 [SMILES: CCOC(=O)Cc1cc2n(c(=O)c1C#N)CCC21OCCO1]

Sodium hydroxide (11.0 g, 276 mmol, 60%) and anhydrous ethanol (5 mL) were added to a mixture of 7'-methyl-5'-oxo-3',5'-dihydro-2'H-spiro[[1,3]dioxolane-2,1'-indolizine]-6'-carbonitrile (32.0 g, 138 mmol), diethyl carbonate (32.6 g, 276 mmol), and dry methylbenzene (500 mL). The mixture was heated to 100° C. and stirred for 3 h. After removal of solvent, the resulting residue was poured into water, and extracted with dichloromethane. The organic layer was washed with brine, dried over anhydrous sodium sulfate, concentrated under vacuum, and purified by column chromatography to afford the title compound (30.2 g, 72%), $^1$H NMR (CDCl$_3$): δ 6.33 (1H, s), 4.22-4.13 (8H, m), 3.78 (2H, s), 2.41 (2H, t, J=7.8 Hz), 1.29 (3H, q, J=7.8 Hz).

Step 6: ethyl 2-bromo-2-(6'-cyano-5'-oxo-3',5'-dihydro-2'H-spiro[[1,3]dioxolane-2,1'-indolizine]-7'-yl)acetate

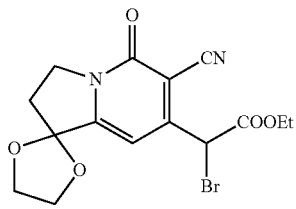 [SMILES: CCOC(=O)C(Br)c1cc2n(c(=O)c1C#N)CCC21OCCO1]

A solution of cold dry bromine (1.56 g, 99 mmol) in glycol dimethyl ether (20 mL) was added dropwise to a mixture of ethyl 2-(6'-cyan-5'-oxo-3',5'-dihydro-2'H-spiro[[1,3]dioxolane-2,1'-indolizine]-7'-yl) acetate (30.2 g, 99 mmol), sodium hydroxide (3.96 g, 99 mmol, 60%), and dry glycol dimethyl ether (300 ml) at 30° C. The reaction solution was stirred for 30 min maintaining the temperature as above, followed by adding once an ice-water mixture (100 mL). The solvent was removed under vacuum, and the residue was poured into water and extracted with dichloromethane. The organic layer was washed with brine, dried over anhydrous sodium sulfate, concentrated under vacuum to afford the title compound (33.6 g, 89%). $^1$H NMR (CDCl$_3$): δ 6.68 (1H, s), 5.60 (1H, s), 4.31-4.14 (8H, m), 2.43 (2H, t, J=7.8 Hz), 3.26 (3H, q, J=7.8 Hz).

Step 7: (2R)-1-(6'-cyano-5'-oxo-3',5'-dihydro-2'H-spiro[[1,3]dioxolane-2,1'-indolizine]-7'-yl)-2-ethoxy-2-oxoethyl 1-tosylpyrrolidine-2-carboxylate

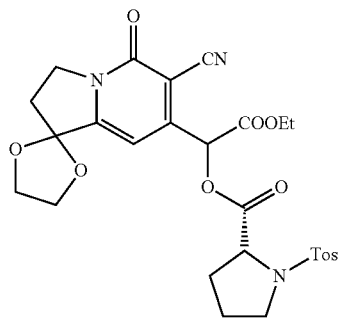

Ethyl 2-bromo-2-(6'-cyano-5'-oxo-3',5'-dihydro-2'H-spiro[[1,3]dioxolane-2,1'-indolizine]-7'-yl)acetate (33.6 g, 88 mmol), (R)-1-p-tosylpyrrolidine-2-carboxylic acid (47.3 g, 176 mmol), and sodium carbonate (18.3 g, 176 mmol) were added to dry N,N-dimethyl formamide (300 mL), and then the mixture was heated to 100° C., and stirred overnight. After removal of solvent, the resulting residue was poured into water, and extracted with dichloromethane. The organic layer was washed with brine, dried over anhydrous sodium sulfate, concentrated under vacuum, and purified by column chromatography to afford the title compound (a mixture of optical isomers at the ratio of about 1:1) (41.7 g, 83%). $^1$H NMR (CDCl$_3$): δ 7.72 (2H, d, J=8.4 Hz), 7.32 (2H, d, J=8.0 Hz), 6.66 (0.5H, s), 6.63 (0.5H, s), 6.31 (0.5H, s), 6.18 (0.5H, s), 4.56-4.53 (0.5H, m), 4.41-4.38 (0.5H, m), 4.34-4.00 (8H, m), 3.62-3.57 (0.5H, m), 3.48-3.43 (0.5H, m), 3.31-3.24 (1H, m), 2.45-2.40 (5H, m), 1.81-1.77 (4H, m), 1.26 (3H, t, J=7.6 Hz).

Step 8: (R)—((S)-2-(6'-cyano-5'-oxo-3',5'-dihydro-2'H-spiro[[1,3]dioxolane-2,1'-indolizine]-7'-yl)-1-ethoxy-1-oxobutan-2-yl) 1-tosylpyrrolidine-2-carboxylate

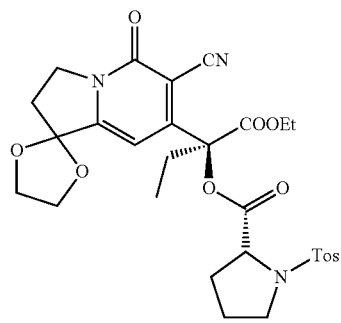

(2R)-1-(6'-cyano-5'-oxo-3',5'-dihydro-2'H-spiro[[1,3]dioxolane-2,1'-indolizine]-7'-yl)-2-ethoxy-2-oxoethyl 1-tosylpyrrolidine-2-carboxylate (11.42 g, 20 mmol), iodoethane (3.43 g, 22 mmol) and sodium hydroxide (840 mg, 21 mmol, 60%) were added to dry N,N-dimethyl formamide (100 mL). The mixture was heated to 30° C., and stirred for 3 h, followed by addition of water (30 mL). After removal of solvent, the resulting residue was poured into water, and extracted by dichloromethane. The organic layer was washed with brine, dried over anhydrous sodium sulfate, concentrated under vacuum, and purified by column chromatography to afford a white solid (6.10 g). The obtained solid was dissolved in isopropanol (450 mL) at 80° C., and cooled to room temperature slowly with crystal precipitation, filtered and the mother liquor was concentrated to give the title compound (2.10 g, 17%, e.e. >95%). $^1$H NMR (CDCl$_3$): δ 7.78 (2H, d, J=8.4 Hz), 7.34 (2H, d, J=8.0 Hz), 6.60 (1H, s), 4.51-4.47 (1H, m), 4.33-4.05 (8H, m), 3.56-3.51 (1H, m), 3.25-3.19 (1H, m), 2.59 (2H, q, J=7.6 Hz), 2.45-2.41 (5H, m), 2.16-1.92 (3H, m), 1.73-1.65 (1H, m), 1.32 (3H, t, J=7.2 Hz), 0.90 (3H, t, J=7.6 Hz).

Step 9: (R)—((S)-2-(6'-(acetamidomethyl)-5'-oxo-3',5'-dihydro-2'H-spiro[[1,3]dioxolane-2,1'-indolizine]-7'-yl)-1-ethoxy-1-oxobutan-2-yl) 1-tosylpyrrolidine-2-carboxylate

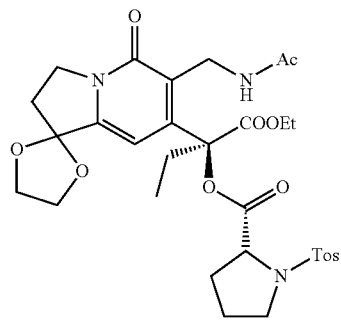

A mixture of (R)—((S)-2-(6'-cyano-5'-oxo-3',5'-dihydro-2'H-spiro[[1,3]dioxolane-2,1'-indolizine]-7'-yl)-1-ethoxy-1-oxobutan-2-yl) 1-tosylpyrrolidine-2-carboxylate (1.0 g, 1.7 mmol), Raney nickel (1.0 g), acetic anhydride (15 mL), and acetic acid (5 mL) was heated to 40° C. under the atmosphere of hydrogen (1.5 atm) and stirred for 4 h. The reaction mixture was filtered, and the filtrate was concentrated and purified by column chromatography to obtain the title compound (890 mg, 82%). $^1$H NMR (CDCl$_3$): δ 7.76 (2H, d, J=8.4 Hz), 7.32 (2H, d, J=8.0 Hz), 7.03 (1H, t, J=4.8 Hz), 6.70 (1H, s), 4.78-4.73 (1H, m), 4.45-4.02 (10H, m), 3.55-3.50 (1H, m), 3.26-3.20 (1H, m), 2.73-2.64 (1H, m), 2.59-2.51 (1H, m), 2.43-2.40 (5H, m), 2.05-1.92 (6H, m), 1.74-1.67 (1H, m), 1.28 (3H, t, J=7.2 Hz), 0.88 (3H, t, J=7.2 Hz).

Step 10: (R)—((S)-2-(6'-(acetoxymethyl)-5'-oxo-3',5'-dihydro-2'H-spiro[[1,3]dioxolane-2,1'-indolizine]-7'-yl)-1-ethoxy-1-oxobutan-2-yl) 1-tosylpyrrolidine-2-carboxylate

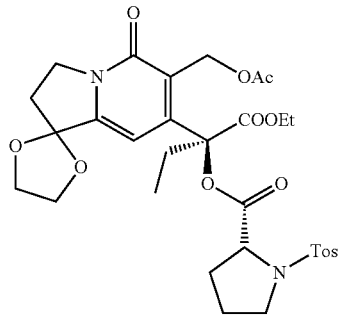

(R)—((S)-2-(6'-acetamidomethyl)-5'-oxo-3',5'-dihydro-2'H-spiro[[1,3]dioxolane-2,1'-indolizine]-7'-yl)-1-ethoxy-1-oxobutan-2-yl) 1-tosylpyrrolidine-2-carboxylate (890 mg, 1.4 mmol) was dissolved in a mixture of acetic anhydride (15 mL) and acetic acid (5 mL). Sodium nitrite (380 mg, 5.5 mmol) was added at 0° C., and then stirred for 4 h with the maintenance of the temperature at 0° C. After filtration, carbon tetrachloride (30 mL) was added to the filtrate, heated to reflux, and reacted overnight. After removal of solvent by concentration, the resulting residue was poured into water, and extracted with ethyl acetate. The organic layer was washed with brine, dried over anhydrous sodium sulfate, concentrated under vacuum, and purified by column chromatography to obtain the title compound (660 mg, 74%). $^1$H NMR (CDCl$_3$): δ 7.75 (2H, d, J=8.0 Hz), 7.34 (2H, d, J=8.0 Hz), 6.78 (1H, s), 5.27 (1H, d, J=11.2 Hz), 5.22 (1H, d, J=11.2 Hz), 4.39-4.06 (9H, m), 3.61-3.56 (1H, m), 3.27-3.22 (1H, m), 2.68-2.62 (1H, m), 2.45-2.33 (6H, m), 2.05-1.92 (6H, m), 1.71-1.67 (1H, m), 1.24 (3H, t, J=7.2 Hz), 0.90 (3H, t, J=7.6 Hz).

Step 11: (S)-4'-ethyl-4'-hydroxy-7',8'-dihydrospiro[[1,3]dioxolane-2,6'-pyrano[3,4-f]indolizine]-3',10'(1'H,4'H)-dione

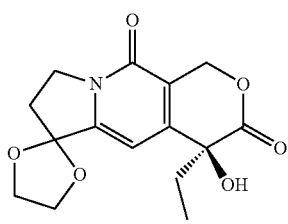 [SMILES: CC[C@@]1(O)C(=O)OCc2c1cc1n(c2=O)CCC12OCCO2]

(R)—((S)-2-(6'-(acetoxymethyl)-5'-oxo-3',5'-dihydro-2'H-spiro[[1,3]dioxolane-2,1'-indolizine]-7'-yl)-1-ethoxy-1-oxobutan-2-yl) 1-tosylpyrrolidine-2-carboxylate (660 mg, 1.0 mmol) and lithium hydroxide hydrate (171 mg, 4.1 mmol) were added to a mixture of methanol (6 mL) and water (2 mL), and stirred at room temperature for 2 h. After removal of methanol by concentration under vacuum, acetic acid (1 mL) and dichloromethane (20 mL) were added. The mixture was stirred at room temperature for 10 h, then concentrated under vacuum, and the resulting residue was purified by column chromatography to obtain the title compound (270 mg, 86%). $^1$H NMR (CDCl$_3$): δ 6.58 (1H, s), 5.60 (1H, d, J=16.4 Hz), 5.17 (1H, d, J=16.4 Hz), 4.21-4.11 (6H, m), 3.77 (1H, s), 2.42 (2H, t, J=6.8 Hz), 1.85-1.75 (2H, m), 0.98 (3H, t, J=7.6 Hz).

Step 12: (S)-4-ethyl-4-hydroxy-7,8-dihydro-1H-pyrano[3,4-f]indolizine-3,6,10(4H)-trione (title compound)

(S)-4'-ethyl-4'-hydroxy-7',8'-dihydrospiro[[1,3]dioxolane-2,6'-pyrano[3,4-f]indolizine]-3',10'(1'H,4'H)-dione (270 mg, 0.88 mmol) and a mixture of trifluoroacetic acid (2 mL) and water (0.5 mL) were stirred under N$_2$ at room temperature for 3 h. After concentration under vacuum, the resulting residue was purified by column chromatography to give the title compound (202 mg, 87%), $^1$H NMR (CDCl$_3$): δ 7.22 (1H, s), 5.68 (1H, d, J=17.2 Hz), 5.24 (1H, d, J=17.2 Hz), 4.36-4.32 (2H, m), 3.65 (1H, s), 2.99-2.95 (2H, m), 1.84-1.78 (2H, m), 0.98 (3H, t, J=7.6 Hz).

Embodiments

All experiments related to water and/or oxygen sensitive reaction were carried out in dry glass instruments under the atmosphere of nitrogen. Unless described otherwise, all raw materials are commercial raw materials, and not involved in any further purification before used.

The silica gel (200-300 mesh) which was used in column chromatography was manufactured by Qingdao Ocean Chemical Factory. The thin-layer chromatography adopted the prepared chromatographic plates (silica gel 60PF254, 0.25 mm) manufactured by E. Merck.

The Nuclear Megnetic Resonance spectrum analysis was carried out by Varian VNMRS-400 resonance spectrometer, wherein tetramethylsilane (TMS=δ 0.00) was used as an internal standard for chemical shifts. The record patterns of $^1$H-NMR spectroscopy data are; proton number, peak shape (s, single peak; d, double peaks; t, triple peaks; m, multiple peaks), coupling constant (in hertz).

The LC-MS analysis employed Angilent LC 1200 Series (5 μm, C18 chromatographic column).

Example 1

(S)-4-ethyl-4-hydroxy-9-methoxy-1H-pyrano[3',4':6,7]indolizino[1,2-b][1,7]naphthyridine-3,14(4H,12H)-dione

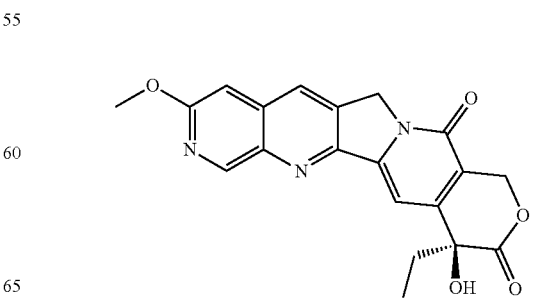

Step 1: 2-methoxypyridine-4-formaldehyde

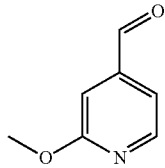

LiAlH$_4$ (1.9 g, 49 mmol) was added portionwise to a solution of 2-methoxy isonicotinic acid (5.0 g, 33 mmol) in tetrahydrofuran (40 mL) at 0° C. The reaction mixture was continuously stirred at 0° C. for 1 h, then saturated sodium sulphate solution was added drop wise slowly. After filtration, the filtrate was extracted with ethyl acetate, and the organic layer was washed with brine, and concentrated under vacuum. The resulting residue was dissolved in dichloromethane (30 mL), and chromium trioxide pyridine (10.6 g, 49 mmol) was added. The resulting mixture was stirred at room temperature for 2 h, then poured onto the short silica gel column and eluted with ethyl acetate. The resulting solution was concentrated under vacuum to remove the solvent. The residue was purified by column chromatography (petroleum ether:ethyl acetate=10:1) to afford the title compound (646 mg, 14%). $^1$H NMR (CDCl$_3$): δ 10.01 (1H, s), 8.36 (1H, d, J=5.2 Hz), 7.29 (1H, dd, J=1.2 Hz, 5.2 Hz), 7.14 (1H, d, J=1.2 Hz), 3.99 (3H, s).

Step 2: 4-(1,3-dioxolane-2-yl)-6-methoxypyridine-3-amine

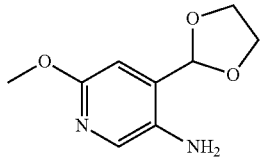

Nitrosonitric acid (1 mL) was added dropwise to a solution of 2-methoxypyridine-4-formaldehyde (137 mg, 1.0 mmol) in trifluoroacetic anhydride (2 mL) at room temperature. The reaction mixture was stirred at 25° C. for 3 days, and then was poured into ice-water mixture, followed by the addition of saturated sodium carbonate solution to adjust the pH value to exceed 10. The resulting mixture was extracted with ethyl acetate, and the organic layer was washed with brine, dried and concentrated. The resulting residue was dissolved in toluene (5 mL), and toluene-p-sulfonic acid (5 mg) and glycol (105 mg, 1.7 mmol) were added. The reaction mixture was heated to reflux and reacted overnight. After cooled, the mixture was washed with saturated sodium carbonate solution and brine, dried, and concentrated under vacuum. The resulting residue was dissolved in methanol (10 mL), added Pd/C catalyst (20 mg), and introduced into hydrogen gas. The reaction system was stirred for 2 h under 1 atm hydrogen, then filtered to remove the catalyst, and concentrated under vacuum to remove the solvent. The residue was purified by column chromatography to obtain the title compound (15 mg, 8%). $^1$H NMR (DMSO-d$_6$): δ 9.31 (1H, s), 8.56 (1H, s), 7.42 (1H, s), 7.34 (1H, s), 6.55 (1H, s), 5.43 (2H, s), 5.30 (2H, s), 4.02 (3H, s), 2.04-1.91 (2H, m), 0.90-0.85 (3H, m).

Step 3: (S)-4-ethyl-4-hydroxy-9-methoxy-1H-pyrano[3',4':6,7]indolizino[1,2-b][1,7]naphthyridine-3,14(4H,12H)-dione (title compound)

(S)-4-ethyl-4-hydroxy-7,8-dihydro-1H-pyrano[3,4-f]indolizine-3,6,10(4H)-trione (13 mg, 0.05 mmol) and toluene-p-sulfonic acid (2 mg) were added to a solution of 4-(1,3-dioxolane-2-yl)-6-methoxypyridine-3-amine (11 mg, 0.05 mmol) in toluene, and nitrogen gas was introduced to the system. The reaction mixture was heated to reflux and reacted for three hours under N$_2$, then the solvent was removed by concentration under vacuum. The resulting residue was purified by high performance liquid chromatography to obtain the title compound (3 mg, 16%). $^1$H NMR (DMSO-d$_6$): δ 9.31 (1H, s), 8.56 (1H, s), 7.42 (1H, s), 7.34 (1H, s), 6.55 (1H, s), 5.43 (2H, s), 5.30 (2H, s), 4.02 (3H, s), 2.04-1.91 (2H, m), 0.90-0.85 (3H, m).

Example 2

(S)-7-ethyl-7-hydroxy-1-methoxy-7H-pyrano[3',4':6,7]indolizino[1,2-b][1,6]naphthyridine-8,11(10H,13H)-dione

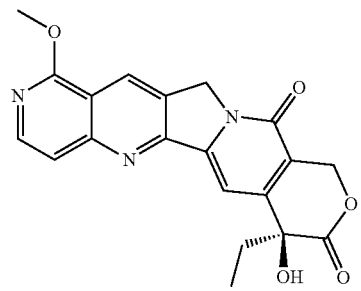 [SMILES: CC[C@@]1(O)C(=O)OCc2c1cc1n(c2=O)Cc2cc3c(OC)nccc3nc2-1]

Step 1: 4-[(ditert-butoxycarbonyl)amino]-2-chloropyridine

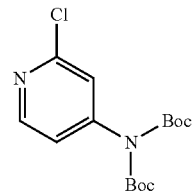 [SMILES: CC(C)(C)OC(=O)N(C(=O)OC(C)(C)C)c1ccnc(Cl)c1]

NaHMDS (9 mL, 2 M, 18 mmol) was added dropwise to a solution of 2-chloro-4-aminopyridine (1.0 g, 7.8 mmol) in dry tetrahydrofuran (30 mL) at 0° C. under N$_2$. After continuously stirred for 30 min, a solution of ditertbutyl dicarbonate (3.75 g, 17 mmol) in dry tetrahydrofuran was added. The reaction mixture was stirred overnight at room temperature, and then poured into saturated ammonium chloride solution. The mixture was extracted with ethyl acetate, and the organic layer was washed by saturated brine, concentrated under vacuum to remove the solvent. The resulting residue was purified by column chromatography (petroleum ether:ethyl acetate=8:1) to afford the title compound (923 mg, 36%). $^1$H NMR (CDCl$_3$): δ 8.39 (1H, d, J=5.2 Hz), 7.19 (1H, d, J=1.6 Hz), 7.05 (1H, dd, J=1.6 Hz, 5.2 Hz), 1.47 (18H, s).

Step 2: tertbutyl 2-chloro-4-(tert-butoxycarbonyl amino) nicotinate

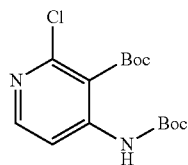

N-butyllithium (11.3 mL, 2.4 M, 27 mmol) was added dropwise to a solution of diisopropylamine (2.74 g, 27 mmol) in dry tetrahydrofuran (50 mL) at 0° C. under $N_2$. After continuously stirred for 30 min and cooled to −60° C., a solution of 4-[(ditert-butoxycarbonyl) amino]-2-chloro-pyridine (2.55 g, 7.8 mmol) in dry tetrahydrofuran was added dropwise. After the reaction mixture was stirred for additional 1 h, saturated ammonium chloride solution was poured in. The resulting mixture was extracted with ethyl acetate, and the organic layer was washed by saturated brine, dried, and concentrated under vacuum to remove the solvent. The resulting residue was purified by column chromatography (petroleum ether:ethyl acetate=10:1) to afford the title compound (1.85 g, 73%), $^1$H NMR (CDCl$_3$): δ 8.72 (1H, s), 8.24-8.20 (2H, m), 1.64 (9H, s), 1.53 (9H, s).

Step 3: methyl 2-methoxy-4-amino nicotinate

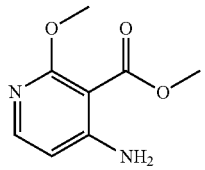

NaH (60%, 120 mg, 3.0 mmol) and methanol (about 0.5 mL) were added to a solution of tertbutyl 2-chloro-4-(tertbutoxycarbonyl amino) nicotinate (330 mg, 1 mmol) in dry toluene (15 mL). The mixture was heated to 100° C. in a sealed tube and stirred for 6 h. After cooled, the reaction mixture was poured onto a short silica gel column, eluted by ethyl acetate, and then concentrated under vacuum to remove the solvent. The resulting residue was purified by column chromatography to obtain the title compound (155 mg, 92%). $^1$H NMR (CDCl$_3$): δ 7.77 (1H, d, J=6.0 Hz), 6.18 (1H, d, J=6.0 Hz), 6.09 (2H, br), 3.95 (3H, s), 3.89 (3H, s).

Step 4: 2-methoxy-4-amino-3-pyridylaldehyde

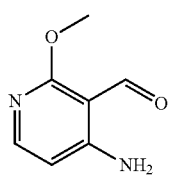

A solution of borane in tetrahydrofuran (0.9 mL, 1 M, 0.9 mmol) was added dropwise to a solution of methyl 2-methoxy-4-amino nicotinate (30 mg, 0.18 mmol) in tetrahydrofuran (3 mL) at 0° C., and the mixture was stirred for 4 h at room temperature. Water (about 1 mL) was added dropwise, and the mixture was then extracted with ethyl acetate. The organic layer was washed with brine, dried, and concentrated under vacuum to remove the solvent. The resulting residue was dissolved in tetrahydrofuran (5 mL), manganese dioxide (42 mg, 0.48 mmol) was added, and the mixture was stirred overnight at room temperature. After filtration, the filtrate was concentrated under vacuum to remove the solvent. The resulting residue was purified by column chromatography (petroleum ether:ethyl acetate=3:1) to afford the title compound (22 mg, 81%). $^1$H NMR (CDCl$_3$): δ 10.31 (1H, s), 7.81 (1H, d, J=6.4 Hz), 6.15 (1H, d, J=6.4 Hz), 3.98 (3H, s).

Step 5: (S)-7-ethyl-7-hydroxy-1-methoxy-7H-pyrano[3',4':6,7]indolizino[1,2-b][1,6]naphthyridine-8,11(10H,13H)-dione (title compound)

Following the similar procedure as step 3 in example 1, 2-methoxy-4-amino-3-pyridylaldehyde and (S)-4-ethyl-4-hydroxy-7,8-dihydro-1H-pyrano[3,4-f]indolizine-3,6,10 (4H)-trione were reacted to produce the title compound. $^1$H NMR (CD$_3$OD): δ 8.86 (1H, s), 7.63 (1H, d, J=7.6 Hz), 7.54 (1H, s), 6.81 (1H, d, J=7.6 Hz), 5.49 (1H, d, J=16.4 Hz), 5.30 (1H, d, J=16.4 Hz), 5.22 (2H, s), 3.56 (3H, s), 1.87-1.84 (2H, m), 0.92-0.88 (3H, m).

Example 3

(S)-7-ethyl-1,7-dihydroxy-7H-pyrano[3',4':6,7]indolizino[1,2-b][1,6]naphthyridine-8,11(10H,13H)-dione

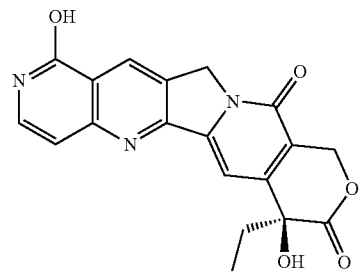 [SMILES: CC[C@@]1(O)C(=O)OCc2c1cc1n(c2=O)Cc2cc3c(O)nccc3nc2-1]

(S)-7-ethyl-1,7-dihydroxy-7H-pyrano[3',4':6,7]indolizino[1,2-b][1,6]naphthyridine-8,11(10H,13H)-dione was a side product at the synthesis procedure of 9-methoxy-10-aza-20 (S)-camptothecin (example 2, step 5), $^1$H NMR (DMSO-d$_6$): δ 11.70 (1H, br), 8.86 (1H, s), 7.54 (1H, dd, J=6.0 Hz, 7.2 Hz), 7.30 (1H, s), 6.75 (1H, d, J=7.2 Hz), 6.54 (1H, s), 5.43 (2H, s), 5.24 (2H, s), 3.89-3.82 (2H, m), 0.88-0.84 (3H, m)

Example 4

(S)-1-(dimethylamino)-7-ethyl-7-hydroxy-7H-pyrano[3',4':6,7]indolizino[1,2-b][1,6]naphthyridine-8,11(10H,13H)-dione

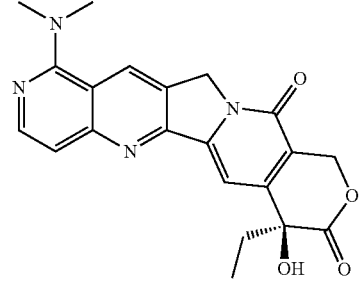 [SMILES: CC[C@@]1(O)C(=O)OCc2c1cc1n(c2=O)Cc2cc3c(N(C)C)nccc3nc2-1]

Step 1: tertbutyl 2-(dimethylamino)-4-(tertbutoxycarbonyl amino) nicotinate

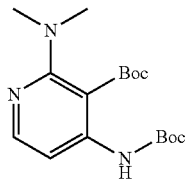

Dimethylamine hydrochloride (490 mg, 6.0 mmol) and triethylamine (1.01 g, 10 mmol) were added to a solution of tertbutyl 2-chloro-4-(tertbutoxycarbonyl amino) nicotinate (657 mg, 2.0 mmol) in DME (10 mL). The reaction solution was heated to 110° C. in a sealed tube, and stirred overnight. After cooled, the reaction mixture was poured into saturated sodium carbonate solution, and extracted with ethyl acetate. The organic layer was combined, washed with brine, and concentrated under vacuum to remove the solvent. The resulting residue was purified by column chromatography (petroleum ether:ethyl acetate=8:1) to obtain the title compound (670 mg, 96%). $^1$H NMR (CDCl$_3$): δ 9.22 (1H, br), 8.03 (1H, d, J=6.4 Hz), 7.55 (1H, d, J=6.4 Hz), 3.00 (6H, s), 1.60 (9H, s), 1.51 (9H, s).

Step 2: tertbutyl 2-(dimethylamino)-4-amino nicotinate

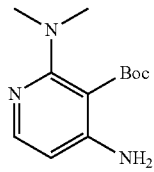

Following the similar procedure as step 3 in example 2, the title compound was synthesized from tertbutyl 2-(dimethylamino)-4-(tertbutoxycarbonyl amino) nicotinate. $^1$H NMR (CDCl$_3$): δ 7.75 (1H, d, J=6.4 Hz), 5.92 (1H, d, J=6.4 Hz), 5.45 (2H, br), 3.01 (6H, s), 1.59 (9H, s).

Step 3: 2-(dimethylamino)-4-amino-3-pyridylaldehyde

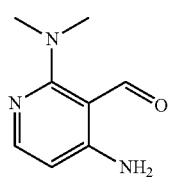

Following the similar procedure as step 4 in example 2, the title compound was synthesized from tertbutyl 2-(dimethylamino)-4-amino nicotinate. $^1$H NMR (CDCl$_3$): δ 9.74 (1H, s), 7.84 (1H, d, J=6.0 Hz), 6.02 (1H, d, J=6.0 Hz), 3.08 (6H, s).

Step 4: (S)-1-(dimethylamino)-7-ethyl-7-hydroxy-7H-pyrano[3',4':6,7]indolizino[1,2-b][1,6]naphthyridine-8,11(10H,13H)-dione (title compound)

Following the similar procedure as step 3 in example 1, the title compound was synthesized from 2-(dimethylamino)-4-amino-3-pyridylaldehyde and (S)-4-ethyl-4-hydroxy-7,8-dihydro-1H-pyrano [3,4-f]indolizine-3,6,10(4H)-trione. $^1$H NMR (CD$_3$OD): δ 9.16 (1H, s), 7.92 (1H, d, J=6.8 Hz), 7.66 (1H, s), 7.48 (1H, d, J=6.8 Hz), 5.58 (1H, d, J=8.8 Hz), 5.41-5.36 (3H, m), 3.56 (6H, s), 1.96-1.93 (2H, m), 1.00-0.96 (3H, m).

Example 5

(S)-7-ethyl-7-hydroxy-2-methoxy-7H-pyrano[3',4':6,7]indolizino[1,2-b][1,5]naphthyridine-8,11(10H,13H)-dione

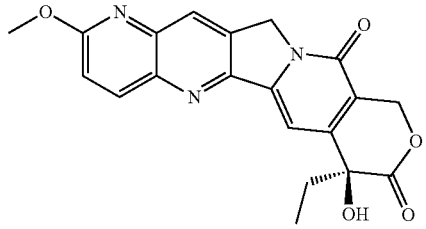 [SMILES: CC[C@@]1(O)C(=O)OCc2c1cc1n(c2=O)Cc2cc3nc(OC)ccc3nc2-1]

Step 1: 6-chloro-3-nitro-pyridine nitrite

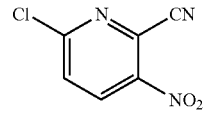 [SMILES: N#Cc1nc(Cl)ccc1[N+](=O)[O-]]

A mixture of 2,6-dichloro-3-nitro-pyridine (3.00 g, 16 mmol), cuprous cyanide (2.87 g, 32 mmol) and N-methylpyrrolidone (10 mL) was stirred at 180° C. for 3 h. The reaction solution was then cooled to room temperature and filtered. The filter cake was washed with ethyl acetate (30 mL) twice, then the ethyl acetate layer was combined, and concentrated under vacuum to afford the title compound (1.10 g, 39%). $^1$H NMR (CDCl$_3$): δ 8.58 (1H, d, J=8.8 Hz), 7.79 (1H, d, J=8.8 Hz).

Step 2: methyl 6-methoxy-3-nitropicolinimidate

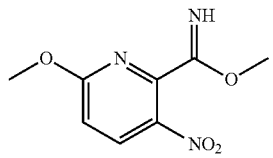

Sodium hydroxide (560 mg, 14 mmol) was added to methanol (30 mL), and stirred at room temperature for 30 min, then 6-chloro-3-nitropyridine nitrile (1.00 g, 5.6 mmol) was added. The reaction solution was stirred at room temperature for 3 h, poured into water, and extracted with dichloromethane. The organic layer was washed with brine, dried, and concentrated under vacuum to obtain the title compound (1.10 g, 93%). $^1$H NMR (CDCl$_3$): δ 8.28 (1H, br), 8.08 (1H, d, J=8.8 Hz), 6.88 (1H, d, J=8.8 Hz), 4.05 (3H, s), 3.92 (3H, s).

Step 3: methyl 6-methoxy-3-nitro-picolinate

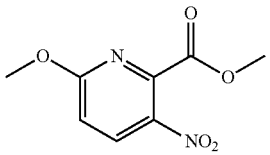

Methyl 6-methoxy-3-nitropicolinimidate (1.10 g, 5.2 mmol) was dissolved in methanol (10 mL), then concentrated hydrochloric acid (3 mL) was added. After the reaction mixture was stirred at room temperature for 6 h, sodium carbonate solution was added to neutralize the mixture. The resulting mixture was extracted with ethyl acetate, and the organic layer was washed by brine, dried, and concentrated under vacuum to obtain the title compound (1.03 g, 93%). $^1$H NMR (CDCl$_3$): δ 8.34 (1H, d, J=9.2 Hz), 6.92 (1H, d, J=9.2 Hz), 4.06 (3H, s), 4.03 (3H, s).

Step 4: methyl 3-amino-6-methoxy picolinate

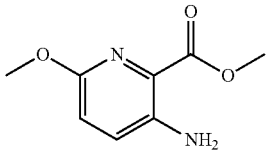

A mixture of methyl 6-methoxy-3-nitro-picolinate (1.03 g, 4.8 mmol), iron powder (1.08 g, 19 mmol), ammonium chloride (389 mg, 7.3 mmol) and ethanol/water (50 mL, 4:1) was stirred at 80° C. for 4 h. After cooled, the mixture was filtered, and the resulting filtrate was poured into water and extracted with ethyl acetate. The organic layer was washed with water, dried, and concentrated under vacuum. The resulting residue was purified by column chromatography to give the title compound (420 mg, 48%), $^1$H NMR (CDCl$_3$): δ 7.05 (1H, d, J=8.8 Hz), 6.81 (1H, d, J=8.8 Hz), 5.46 (2H, br), 3.94 (3H, s), 3.92 (3H, s).

Step 5: (3-amino-6-methoxypyridine-2-yl) methanol

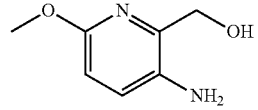

LiAlH$_4$ (262 mg, 6.9 mmol) was added to a solution of methyl 3-amino-6-methoxy picolinate (420 mg, 2.3 mmol) in tetrahydrofuran (10 mL) at 0° C. The mixture was stirred at 0° C. for 1 h, and then saturated sodium sulfate solution was added dropwise. The reaction solution was continuously stirred for 2 h, followed by filtration. The filtrate was extracted with ethyl acetate, and the organic layer was washed by brine, dried, and concentrated under vacuum. The resulting residue was purified by column chromatography to obtain the title compound (170 mg, 48%). $^1$H NMR (CDCl$_3$): δ 7.04-7.02 (1H, m), 6.56 (1H, d, J=8.4 Hz), 4.61 (2H, s), 3.90 (3H, s), 3.39 (2H, br).

Step 6: 3-amino-6-methoxy-pyridylaldehyde

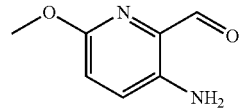

A mixture of (3-amino-6-methoxypyrid-2-yl) methanol (154 mg, 1.0 mmol), manganese dioxide (522 mg, 6.0 mmol) and dichloromethane (10 mL) was stirred at room temperature for 6 h. After filtration, the filter cake was washed with dichloromethane, and the organic layer was combined and concentrated under vacuum. The resulting residue was purified by column chromatography to give the title compound (28 mg, 18%). $^1$H NMR (CDCl$_3$): δ 9.92 (1H, s), 7.01 (1H, d, J=8.8 Hz), 6.79 (1H, d, J=8.8 Hz), 5.82 (2H, br), 3.90 (3H, s).

Step 7: (S)-7-ethyl-7-hydroxy-2-methoxy-7H-pyrano[3',4':6,7]indolizino[1,2-b][1,5]naphthyridine-8,11(10H,13H)-dione (title compound)

A mixture of 3-amino-6-methoxy-pyridylaldehyde (10 mg, 0.066 mmol), (S)-4-ethyl-4-hydroxy-7,8-dihydro-1H-pyrano[3,4-f]indolizine-3,6,10(4H)-trione (17 mg, 0.066 mmol), toluene-p-sulfonic acid (2 mg) and dry toluene (5 mL) was refluxed under N$_2$ for 3 h. The reaction solution was concentrated under vacuum, and methanol (10 mL) was added to the resulting residue, which was then stirred at room temperature for 30 min. The mixture was filtered and the solid was washed by methanol, which was dried to give the title compound (12 mg, 49%). $^1$H NMR (DMSO-d$_6$): δ 8.49 (1H, s), 8.42 (1H, d, J=9.2 Hz), 7.38 (1H, d, J=9.2 Hz), 7.28 (1H, s), 6.51 (1H, s), 5.42 (2H, s), 5.28 (2H, s), 4.05 (3H, s), 1.89-1.82 (2H, m), 0.88-0.85 (3H, m).

Example 6

(S)-7-ethyl-7-hydroxy-10,13-dihydro-2H-furo[2,3-g]pyrano[3',4':6,7]indolizino [1,2-b]quinoline-8,11 (3H,7H)-dione

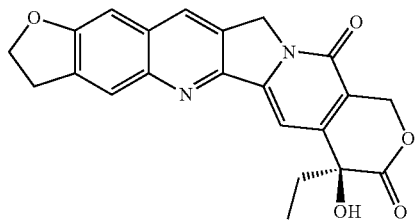 [SMILES: CC[C@@]1(O)C(=O)OCc2c1cc1n(c2=O)Cc2cc3cc4c(cc3nc2-1)CCO4]

Step 1: 2-(2,5-dibromophenoxy) ethanol

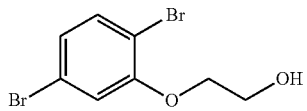

A mixture of 1,4-dibromo-2-fluorobenzene (6.86 g, 27 mmol), ethanediol (35 mL), N-methylpyrrolidone (35 mL) and potassium tert-butoxide (11.2 g, 95 mmol) was stirred at 100° C. overnight under N₂. After the mixture was cooled to room temperature, water (15 mL) was added slowly within 30 min. Then the mixture was filtered, and the filter cake was washed by ethanediol. To the filtrate was added water and the mixture was stirred for 30 min. The resulting solution was then cooled to 15° C. and let stay for 1 h. The precipitate was filtered, washed by water, and dried to give the title compound (4.70 g, 59%). $^1$H NMR (CDCl₃): δ 7.40 (1H, d, J=8.4 Hz), 7.05 (1H, d, J=2.4 Hz), 7.02-6.70 (1H, m), 4.14 (2H, t, J=4.4 Hz), 4.02-3.98 (2H, m), 2.13 (1H, t, J=6.4 Hz).

Step 2: 1,4-dibromo-2-(2-bromoethoxy) benzene

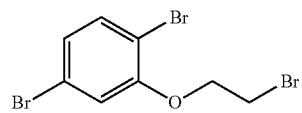 [SMILES: BrCCOc1cc(Br)ccc1Br]

To a solution of 2-(2,5-dibromophenoxy) ethanol (2.00 g, 6.8 mmol) in toluene (20 mL) was added phosphorus tribromide (2.01 g, 7.4 mmol). The mixture was heated to 90° C. and stirred for 10 h, then cooled to room temperature. 1 N sodium hydroxide solution was added slowly to quench the reaction. The organic layer was washed by water, dried, and concentrated under vacuum to give the title compound (2.13 g, 88%). $^1$H NMR (CDCl₃): δ 7.41 (1H, d, J=9.2 Hz), 7.04-7.01 (2H, m), 4.33 (2H, t, J=6.4 Hz), 3.68 (2H, t, J=6.4 Hz).

Step 3: 6-bromo-2,3-dihydrobenzofuran

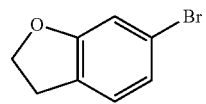

To a solution of 1,4-dibromo-2-(2-bromoethoxy) benzene (2.13 g, 5.9 mmol) in benzene/tetrahydrofuran (28 mL, 2:5) at −78° C. under N₂ was added n-butyllithium (2.5 mL, 6.1 mmol). The mixture was stirred at −78° C. for 1 h, and quenched by acetic acid. Water was added, and the organic layer was separated, dried, and concentrated under vacuum to give the title compound (1.00 g, 85%). $^1$H NMR (CDCl₃): δ 7.03 (1H, d, J=8.0 Hz), 6.91-6.93 (2H, m), 4.58 (2H, t, J=4.8 Hz), 3.15 (2H, t, J=4.8 Hz).

Step 4: 2,3-dihydrobenzofuran-6-formaldehyde

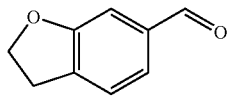

A solution of 6-bromo-2,3-dihydrobenzofuran (1.00 g, 5.0 mmol) in dry tetrahydrofuran (20 mL) was cooled to −78° C., and then n-butyllithium (2.3 mL, 2.4 M, 5.5 mmol) was added under N₂. The reaction solution was stirred at −78° C. for 30 min, and then dry N,N-dimethyl formamide (731 mg, 10 mmol) was added dropwise. Then the reaction solution was stirred at −78° C. for 1 h, and quenched by saturated ammonium chloride solution. The mixture was extracted with ethyl acetate, and the organic layer was separated, dried, and concentrated to give the title compound (384 mg, 52%). $^1$H NMR (CDCl₃): δ 9.92 (1H, s), 7.40-7.33 (2H, m), 4.64 (2H, t, J=8.8 Hz), 3.31-3.26 (2H, m).

Step 5: 5-amino-2,3-dihydrobenzofuran-6-formaldehyde

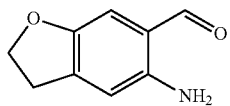

2,3-Dihydrobenzofuran-6-formaldehyde (249 mg, 1.7 mmol) was added to concentrated nitric acid (5 mL). The mixture was stirred at room temperature for 2 h, poured into ice-water, and extracted with ethyl acetate. The extract was washed by brine and concentrated under vacuum. To the resulting residue were added ethanol/water (12 mL, 5:1) mixture, iron powder (290 mg, 5.2 mmol) and ammonium chloride (104 mg, 1.9 mmol). The mixture was stirred at 80° C. for 2 h, and filtered. The filtrate was concentrated, and the resulting residue was purified by column chromatography to give the title compound (56 mg, 27%). $^1$H NMR (CDCl₃): δ 9.75 (1H, s), 6.84 (1H, s), 6.57 (1H, s), 5.89 (2H, br), 4.52 (2H, t, J=8.4 Hz), 3.19-3.15 (2H, m).

Step 6: (S)-7-ethyl-7-hydroxy-10,13-dihydro-2H-furo[2,3-g]pyrano[3',4':6,7]indolizino [1,2-b]quinoline-8,11(3H,7H)-dione (title compound)

To dry toluene (5 mL) were added 5-amino-2,3-dihydrobenzofuran-6-formaldehyde (35 mg, 0.22 mmol), (S)-4-ethyl-4-hydroxy-7,8-dihydro-1H-pyrano[3,4-f]indolizine-3,6,10(4H)-trione (37 mg, 0.14 mmol), and toluene-p-sulfonic acid (3 mg). The reaction solution was refluxed under N₂ for 3 h and concentrated in vacuo. The resulting residue was purified by preparative high performance liquid chromatography to afford the title compound (7 mg, 13%). $^1$H NMR (DMSO-d₆): δ 8.45 (1H, s), 8.00 (1H, s), 7.33 (1H, s), 7.26 (1H, s), 6.51 (1H, s), 5.41 (2H, s), 5.23 (2H, s), 4.71 (2H, t, J=8.0 Hz), 3.47 (2H, t, J=8.0 Hz), 1.99-1.86 (2H, m), 0.90-0.85 (3H, m).

Example 7

(S)-4-ethyl-4,8-dihydroxy-9-methoxy-1H-pyrano[3',4':6,7]indolizino[1,2-b]quinoline-3,14(4H,12H)-dione

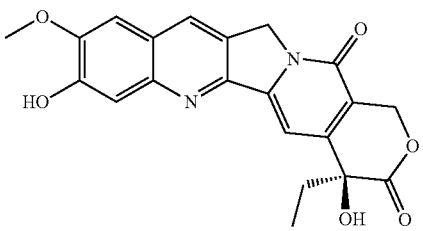 [SMILES: CC[C@@]1(O)C(=O)OCc2c1cc1n(c2=O)Cc2cc3cc(OC)c(O)cc3nc2-1]

Step 1: 4-(benzyloxy)-3-methoxy benzaldehyde

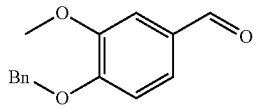

4-Hydroxy-3-methoxy benzaldehyde (2.0 g, 12.8 mmol), benzyl bromide (2.2 g, 12.8 mmol) and potassium carbonate (880 mg, 6.4 mmol) were added to acetone (30 mL), and the mixture was refluxed overnight. Water was added, and the mixture was filtered. The filter cake was washed by water, and recrystallized in ethanol to give the title compound (3.1 g, 99%). $^1$H NMR (CDCl$_3$): δ 9.84 (1H, s), 7.45-7.31 (7H, m), 6.99 (1H, d, J=8.4 Hz), 5.25 (2H, s), 3.95 (3H, s).

Step 2: 4-(benzyloxy)-5-methoxy-2-nitro-benzaldehyde

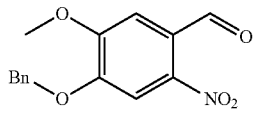

To concentrated nitric acid (3 mL) was added 4-(benzyloxy)-3-methoxy benzaldehyde (242 mg, 1.0 mmol). The mixture was stirred at 0° C. for 1 h and then filtered. The filter cake was washed with water and dried to give the title compound (280 mg, 97%). $^1$H NMR (CDCl$_3$): δ 10.45 (1H, s), 7.68 (1H, s), 7.48-7.35 (7H, m), 5.28 (2H, s), 4.03 (3H, s).

Step 3: 2-amino-4-hydroxy-5-methoxy benzaldehyde

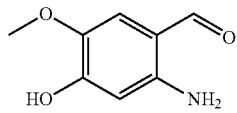

A mixture of 4-(benzyloxy)-5-methoxy-2-nitro-benzaldehyde (280 mg, 0.97 mmol) and acetic acid (3 mL) was heated to 85° C., and then hydrobromic acid (48%, 1 mL) was added. The reaction mixture was stirred at 85° C. for 1 h. After cooled, water was added, and the resulting mixture was extracted with ethyl acetate. The organic layer was washed by brine, dried, and concentrated in vacuo. To the resulting residue were added ethanol/water (10 mL, 4:1), iron powder (212 mg, 3.8 mmol) and ammonium chloride (76 mg, 1.4 mmol). The mixture was stirred at 80° C. for 30 min, and then filtered. Water was added to the filtrate, and the resulting mixture was extracted with ethyl acetate. The organic layer was washed with brine, dried, and concentrated under vacuum. The resulting residue was purified by column chromatography to give the title compound (62 mg, 52%). $^1$H NMR (CDCl$_3$): δ 9.67 (1H, s), 6.86 (1H, s), 6.22 (1H, s), 6.20 (1H, br), 6.03 (2H, br), 3.89 (3H, s)

Step 4: (S)-4-ethyl-4,8-dihydroxy-9-methoxy-1H-pyrano[3',4':6,7]indolizino[1,2-b]quinoline-3,14(4H,12H)-dione (title compound)

A mixture of 2-amino-4-hydroxy-5-methoxy benzaldehyde (19 mg, 0.31 mmol), (S)-4-ethyl-4-hydroxy-7,8-dihydro-1H-pyrano[3,4-f]indolizine-3,6,10(4H)-trione (26 mg, 0.1 mmol), toluene-p-sulfonic acid hydrate (3 mg) and dry toluene (3 mL) was heated to 90° C. under N$_2$, and stirred for 2 h. After the removal of solvent by concentration in vacuo, methanol (10 mL) was added to the residue. The mixture was stirred at room temperature for 30 min, and filtered. The filter cake was washed by methanol and dried to give the title compound (19 mg, 48%). $^1$H NMR (DMSO-d$_6$): δ 10.30 (1H, br), 8.41 (1H, s), 7.44 (1H, s), 7.37 (1H, s), 7.23 (1H, s), 6.49 (1H, s), 5.40 (2H, s), 5.21 (2H, s), 3.94 (3H, s), 1.97-1.84 (2H, m), 0.89-0.82 (3H, m).

Example 8

(S)-4-ethyl-8-fluoro-4,9-dihydroxy-1H-pyrano[3',4':6,7]indolizino[1,2-b]quinoline-3,14(4H,12H)-dione

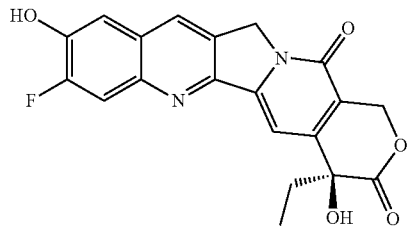 [SMILES: CC[C@@]1(O)C(=O)OCc2c1cc1n(c2=O)Cc2cc3cc(O)c(F)cc3nc2-1]

Step 1: (4-fluoro-3-methoxyphenyl) methanol

To a solution of methyl 4-fluoro-3-methoxy benzoate (8.3 g, 45 mmol) in tetrahydrofuran (30 mL), LiAlH$_4$ (3.42 g, 90 mmol) was added. The reaction mixture was stirred at 0° C. for 1 h, and then saturated sodium sulfate solution was added dropwise. The mixture was filtered, and the filtrate was concentrated under vacuum to give the title compound (7.1 g, 100%). ¹H NMR (CDCl₃): δ 7.06-7.00 (2H, m), 6.81-6.83 (1H, m), 4.63 (2H, s), 3.89 (3H, s), 1.90 (1H, s).

Step 2: 4-fluoro-3-methoxy benzaldehyde

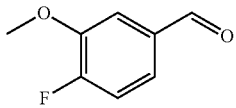

To a solution of (4-fluoro-3-methoxyphenyl) methanol (1.56 g, 10 mmol) in dichloromethane (40 mL) was added chromium trioxide pyridine (4.31 g, 20 mmol). The mixture was stirred at room temperature for 30 min and filtered. The filtrate was poured onto a short silica gel column, and eluted with dichloromethane. The resulting solution was concentrated under vacuum to afford the title compound (1.25 g, 81%). ¹H NMR (CDCl₃): δ 9.92 (1H, s), 7.52 (1H, dd, J=2.0 Hz, 8.4 Hz), 7.47-7.43 (1H, m), 7.26-7.22 (1H, m), 3.96 (3H, s).

Step 3: 2-amino-4-fluoro-5-hydroxy benzaldehyde

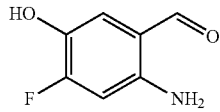

To a solution of 4-fluoro-3-methoxy benzaldehyde (770 mg, 5.0 mmol) in concentrated sulfuric acid (10 mL) at 0° C. was added fuming nitric acid (95%, 315 mg, 4.8 mmol) dropwise. The reaction mixture was stirred at room temperature for 1 h, then poured into iced water, and filtered. The filter cake was washed by water and then dried. The resulting residue was dissolved in N,N-dimethyl formamide (20 mL), followed by addition of lithium chloride (1.60 g, 25 mmol). The mixture was refluxed for 4 h, then poured into water, and concentrated hydrochloric acid was added dropwise to pH <4, followed by extraction with ethyl acetate. The organic layer was washed with brine, dried, and concentrated in vacuo. To the resulting residue were added ethanol/water (25 mL, 4:1), iron powder (1.21 g, 22 mmol) and ammonium chloride (433 mg, 8.1 mmol). The mixture was stirred at 80° C. for 2 h, and filtered. Water was added to the filtrate, and the resulting mixture was extracted with ethyl acetate. The organic layer was washed by brine, dried, and concentrated under vacuum. The resulting residue was purified by column chromatography to give the title compound (125 mg, 16%). ¹H NMR (CDCl₃): δ 9.75 (1H, s), 7.14 (1H, d, J=9.6 Hz), 6.41 (1H, d, J=12.0 Hz), 5.96 (2H, br), 4.58 (1H, d, J=3.6 Hz).

Step 4: (S)-4-ethyl-8-fluoro-4,9-dihydroxy-1H-pyrano[3',4':6,7]indolizino[1,2-b]quinoline-3,14(4H,12H)-dione (title compound)

A mixture of 2-amino-4-fluoro-5-hydroxy benzaldehyde (33 mg, 0.21 mmol), (S)-4-ethyl-4-hydroxy-7,8-dihydro-1H-pyrano[3,4-f]indolizine-3,6,10(4H)-trione (37 mg, 0.14 mmol), toluene-p-sulfonic acid (3 mg) and dry toluene (5 mL) was refluxed under N₂ for 3 h. The reaction mixture was then concentrated under vacuum, and the resulting residue was purified by preparative HPLC to obtain the title compound (5 mg, 10%), ¹H NMR (DMSO-d₆): δ 11.01 (1H, s), 8.53 (1H, s), 7.93 (1H, d, J=12.4 Hz), 7.49 (1H, d, J=9.6 Hz), 7.27 (1H, s), 6.51 (1H, s), 5.42 (2H, s), 5.24 (2H, s), 1.86-1.84 (2H, m), 0.89-0.86 (3H, m).

Example 9

(S)-4-ethyl-8-fluoro-4-hydroxy-9-methoxy-1H-pyrano[3',4':6,7]indolizino[1,2-b]quinoline-3,14(4H,12H)-dione

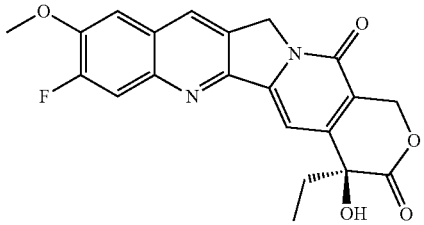 [SMILES: CC[C@@]1(O)C(=O)OCc2c1cc1n(c2=O)Cc2cc3cc(OC)c(F)cc3nc2-1]

Step 1: 2-amino-4-fluoro-5-methoxy benzaldehyde

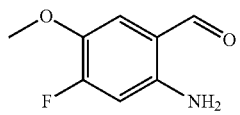

To a solution of 4-fluoro-3-methoxy benzaldehyde (770 mg, 5.0 mmol) in concentrated sulfuric acid (10 mL) was added fuming nitric acid (95%, 315 mg, 4.8 mmol) dropwise. The reaction mixture was stirred at room temperature for 1 h, and then poured into iced water, followed by filtration. The filter cake was washed by water and dried. To the resulting residue were added ethanol/water (25 mL, 4:1), iron powder (1.12 g, 20 mmol) and ammonium chloride (404 mg, 7.6 mmol). The mixture was stirred at 80° C. for 2 h, and then filtered. To the filtrate was added water, and the mixture was then extracted with ethyl acetate. The organic layer was washed with brine, dried, and concentrated under vacuum. The resulting residue was purified by column chromatography to give the title compound (180 mg, 21%). ¹H NMR (CDCl₃): δ 9.78 (1H, s), 7.04 (1H, d, J=9.2 Hz), 6.41 (1H, ds J=11.6 Hz), 6.03 (2H, br), 3.86 (1H, s).

Step 2: (S)-4-ethyl-8-fluoro-4-hydroxy-9-methoxy-1H-pyrano[3',4': 6,7]indolizino[1,2-b]quinoline-3,14 (4H,12H)-dione (title compound)

A mixture of 2-amino-4-fluoro-5-methoxy benzaldehyde (34 mg, 0.20 mmol), (S)-4-ethyl-4-hydroxy-7,8-dihydro-1H-pyrano[3,4-f]indolizine-3,6,10(4H)-trione (34 mg, 0.13 mmol), toluene-p-sulfonic acid (3 mg) and dry toluene (6 mL) was refluxed under N₂ for 3 h. The reaction mixture was then concentrated under vacuum, and the resulting residue was washed by methanol and dried to obtain the title compound (40 mg, 78%). ¹H NMR (DMSO-d₆): δ 8.58 (1H, s), 7.96 (1H, d, J=12.4 Hz), 7.74 (1H, d, J=8.8 Hz), 7.27 (1H, s), 6.51 (1H, s), 5.40 (2H, s), 5.26 (2H, s), 1.86-1.82 (2H, m), 0.87-0.83 (3H, m).

Example 10

(S)-4-ethyl-4,7-dihydroxy-8-methoxy-1H-pyrano[3', 4':6,7]indolizino[1,2-b]quinoline-3,14(4H,12H)-dione

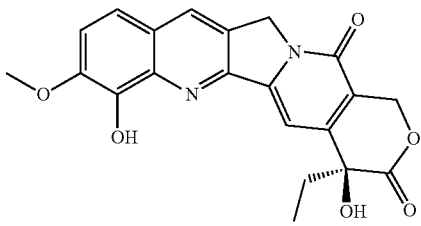 [SMILES: CC[C@@]1(O)C(=O)OCc2c1cc1n(c2=O)Cc2cc3ccc(OC)c(O)c3nc2-1]

Step 1: 2-amino-3-hydroxy-4-methoxy benzaldehyde

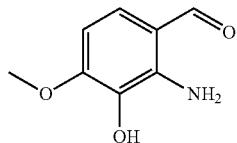

To a solution of 3-hydroxy-4-methoxy benzaldehyde (456 mg, 3.0 mmol) in acetic acid (10 mL) was added concentrated nitric acid (65%, 290 mg, 3.0 mmol) dropwise. The reaction mixture was stirred at room temperature for 2 h, and then poured into water, followed by extraction with ethyl acetate. The organic layer was washed by brine, dried, and concentrated under vacuum. To the resulting residue were added ethanol/water (50 mL, 4:1), iron powder (672 mg, 12 mmol) and ammonium chloride (636 mg, 12 mmol). The mixture was stirred at 80° C. for 1 h, and then filtered. To the filtrate was added water, and the mixture was then extracted with ethyl acetate. The organic layer was washed with brine, dried, and concentrated in vacuo. The resulting residue was purified by column chromatography to give the title compound (140 mg, 28%). $^1$H NMR (CDCl$_3$): δ 9.77 (1H, s), 7.09 (1H, d, J=8.8 Hz), 6.40 (1H, d, J=8.8 Hz), 5.37 (2H, br), 5.06 (1H, br), 3.95 (3H, s).

Step 2: (S)-4-ethyl-4,7-dihydroxy-8-methoxy-1H-pyrano[3',4':6,7]indolizino[1,2-b]quinoline-3,14(4H, 12H)-dione (title compound)

A mixture of 2-amino-3-hydroxy-4-methoxy benzaldehyde (19 mg, 0.11 mmol), (S)-4-ethyl-4-hydroxy-7,8-dihydrog-1H-pyrano[3,4-f]indolizine-3,6,10(4H)-trione (26 mg, 0.1 mmol), toluene-p-sulfonic acid (1 mg) and dry toluene (5 mL) was heated to 90° C. under N$_2$, and stirred for 2 h. The reaction mixture was then concentrated under vacuum, and methanol (10 mL) was added to the residue. The resulting mixture was stirred at room temperature for 30 min. After filtration, the filter cake was washed with methanol and dried to obtain the title compound (17 mg, 43%). $^1$H NMR (DMSO-d$_6$): δ 9.50 (1H, br), 8.54 (1H, s), 7.56-7.55 (2H, m), 6.54-6.53 (1H, m), 5.41 (2H, s), 5.23 (2H, s), 3.94 (3H, s), 1.97-1.84 (2H, m), 0.89-0.82 (3H, m).

Example 11

(S)-11-amino-4-ethyl-8-fluoro-4-hydroxy-9-methoxy-1H-pyrano[3',4':6,7]indolizino[1,2-b]quinoline-3,14(4H,12H)-dione

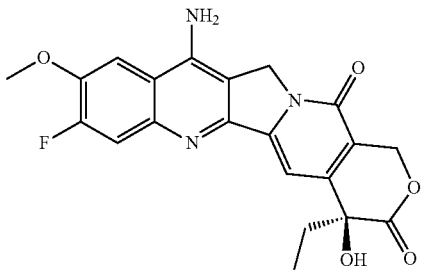 [SMILES: CC[C@@]1(O)C(=O)OCc2c1cc1n(c2=O)Cc2c-1nc1cc(F)c(OC)cc1c2N]

Step 1: 4-fluoro-5-methoxy-2-nitro-benzoic acid

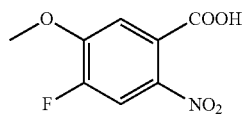

To a solution of 4-fluoro-3-methoxy benzoic acid (3.40 mg, 20 mmol) in concentrated sulfuric acid (25 mL) at 0° C. was added potassium nitrate (202 mg, 20 mmol), and the mixture was stirred at 40° C. for 2 h. After cooled to room temperature, the mixture was poured into ice water, and extracted with ethyl acetate. The organic layer was washed with brine, dried, and concentrated under vacuum. The resulting residue was purified by column chromatography to give the title compound (1.81 g, 42%). $^1$H NMR (DMSO-d$_6$): δ 8.08-8.05 (1H, m), 7.49-7.47 (1H, m), 3.95 (3H, s).

Step 2: 4-fluoro-5-methoxy-2-nitro-benzamide

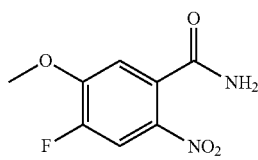

To a mixture of SOCl$_2$/CHCl$_3$ (10 mL, 1:2) was added 4-fluoro-5-methoxy-2-nitro-benzoic acid (860 mg, 4.0 mmol), and the reaction solution was heated to 65° C. and stirred overnight. After concentration in vacuo, the resulting residue was dissolved in dry EtOAc (30 mL), and ammonia gas was introduced for 15 min at 0° C. The resulting mixture was washed by saturated sodium carbonate solution, and the organic layer was washed by brine, dried, and concentrated under vacuum to give the title compound (856 mg, 100%), $^1$H NMR (CDCl$_3$): δ 8.08-8.02 (1H, m), 7.70 (1H, br), 7.33-7.31 (1H, m), 3.93 (3H, s).

Step 3: 4-fluoro-5-methoxy-2-nitro-cyanophenyl

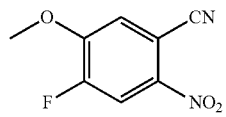

To a mixture of trifluoroacetic anhydride/dichloromethane (10 mL, 1:2) was added 4-fluoro-5-methoxy-2-nitrobenzamide (856 mg, 4.0 mmol), and the reaction solution was stirred at room temperature for 4 h. Water was added, and the mixture was extracted with dichloromethane. The organic layer was washed by brine, dried, and concentrated under vacuum. The resulting residue was purified by column chromatography to obtain the title compound (675 mg, 86%). $^1$H NMR (DMSO-$d_6$): δ 8.12-8.09 (1H, m), 7.40-7.38 (1H, m), 4.11 (3H, s).

Step 4: 2-amino-4-fluoro-5-methoxy-cyanophenyl

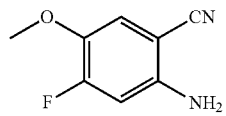

To a mixture of ethanol/water (30 mL, 1:1) were added 4-fluoro-5-methoxy-2-nitro-cyanophenyl (196 mg, 1.0 mmol) and sodium hydrosulfite (522 mg, 3.0 mmol), and the reaction solution was heated to 80° C. and stirred for 2 h. After concentration in vacuo, water was added, and the mixture was extracted with ethyl acetate. The organic layer was washed by brine, dried, and concentrated under vacuum. The resulting residue was purified by column chromatography to give the title compound (130 mg, 78%). $^1$H NMR (CDCl$_3$): δ 6.95-6.93 (1H, m), 6.53-6.50 (1H, m), 4.23 (2H, br), 3.82 (3H, s).

Step 5: (S)-11-amino-4-ethyl-8-fluoro-4-hydroxy-9-methoxy-1H-pyrano[3',4':6,7]indolizino[1,2-b]quinoline-3,14(4H,12H)-dione (title compound)

A mixture of 2-amino-4-fluoro-5-methoxy-cyanophenyl (18 mg, 0.11 mmol), (S)-4-ethyl-4-hydroxy-7,8-dihydro-1H-pyrano[3,4-f]indolizine-3,6,10(4H)-trione (26 mg, 0.10 mmol), toluene-p-sulfonic acid (1 mg) and dry toluene (5 mL) was refluxed under N$_2$ for 24 h. The reaction mixture was concentrated under vacuum, and the resulting residue was purified by preparative HPLC to obtain the title compound (3 mg, 7%). $^1$H NMR (DMSO-$d_6$): δ 8.10 (1H, br), 7.91-7.89 ($^1$H, m), 7.68-7.65 (1H, m), 7.31 (1H, s), 6.50 (1H, br), 5.39 (2H, s), 5.01 (2H, m), 3.85 (3H, s), 1.97-1.84 (2H, m), 0.89-0.82 (3H, m).

Example 12

(S)-4-ethyl-8-fluoro-4-hydroxy-9-methoxy-11-methyl-1H-pyrano[3',4':6,7]indolizino[1,2-b]quinoline-3,14(4H,12H)-dione

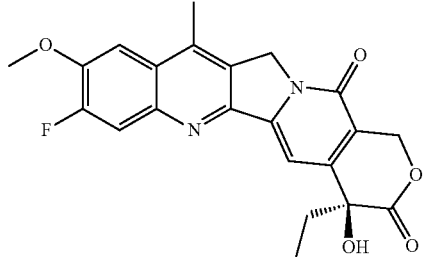 [SMILES: CC[C@@]1(O)C(=O)OCc2c1cc1n(c2=O)Cc2c-1nc1cc(F)c(OC)cc1c2C]

Step 1: 4-fluoro-N,3-dimethoxy-N-methyl-benzamide

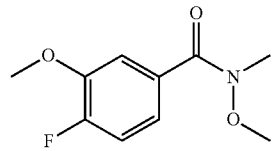

To a solution of 4-fluoro-3-methoxy-benzoic acid (1.7 g, 10 mmol) and N,O-dimethyl-hydroxylamine hydrochloride (1.17 g, 12 mmol) in dichloromethane (20 mL) were added triethylamine (7.0 mL, 50 mmol) and EDCI (2.11 g, 11 mmol). The reaction solution was stirred at room temperature for 36 h, then poured into water (30 mL), and extracted with dichloromethane. The organic layer was washed by brine, and concentrated in vacuo. The resulting residue was purified by column chromatography to give the title compound (628 mg, 29%). $^1$H NMR (CDCl$_3$): δ 7.37-7.35 (1H, m), 7.32-7.28 (1H, m), 7.10-7.05 (1H, m), 3.91 (3H, s), 3.55 (3H, s), 3.36 (3H, s).

Step 2: 4-fluoro-3-methoxy-acetophenone

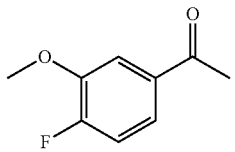

A solution of 4-fluoro-N,3-dimethoxy-N-methylbenzamide (628 mg, 2.9 mmol) in tetrahydrofuran (5 mL) was cooled to 0° C. Methyl magnesium bromide solution (3.2 mL, 4.4 mmol) was added dropwise under N$_2$. The mixture was stirred at 0° C. for 15 min, and then quenched with saturated ammonium chloride solution. The resulting mixture was extracted with ethyl acetate. The organic layer was washed by brine, dried, and the solvent was removed under vacuum to give the title compound (465 mg, 94%). $^1$H NMR (CDCl$_3$): δ 7.64-7.61 (1H, m), 7.55-7.52 (1H, m), 7.17-7.12 (1H, m), 3.96 (3H, s), 2.60 (3H, s).

Step 3: 4-fluoro-5-methoxy-2-nitro-acetophenone

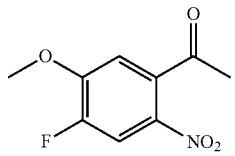

4-Fluoro-3-methoxy acetophenone (465 mg, 2.8 mmol) was dissolved in concentrated sulfuric acid (3 mL), cooled to 0° C., and then fuming nitric acid (183 mg, 2.8 mmol) was added dropwise. The reaction solution was continuously stirred at 0° C. for 0.5 h, then poured into water. The resulting mixture was extracted with ethyl acetate. The organic layer was washed by brine, dried, and concentrated in vacuo to afford the title compound (435 mg, 74%). $^1$H NMR (CDCl$_3$): δ 7.94 (1H, d, J=10.4 Hz), 6.87 (1H, d, J=8.0 Hz), 4.02 (3H, s), 2.54 (3H, s).

Step 4: 2-amino-4-fluoro-5-methoxy-acetophenone

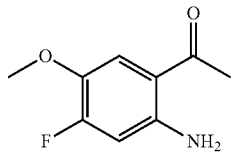

A mixture of 4-fluoro-5-methoxy-2-nitro-acetophenone (435 mg, 2.0 mmol), ammonium chloride (164 mg, 3.0 mmol) and, iron powder (456 mg, 8.2 mmol) was refluxed in ethanol/water (20 mL, 4:1) for 3 h, and then filtered. The filtrate was poured into water (30 mL), and extracted with ethyl acetate. The organic layer was washed by brine, and concentrated in vacuo. The resulting residue was purified by column chromatography to give the title compound (271 mg, 72%). $^1$H NMR (CDCl$_3$): δ 7.26 (1H, d, J=9.2 Hz), 6.39 (1H, d, J=12.8 Hz), 6.18 (2H, br), 3.85 (3H, s), 2.54 (3H, s).

Step 5: (S)-4-ethyl-8-fluoro-4-hydroxy-9-methoxy-11-methyl-1H-pyrano[3',4':6,7]indolizino[1,2-b]quinoline-3,14(4H,12H)-dione (title compound)

To a solution of 2-amino-4-fluoro-5-methoxy acetophenone (13 mg, 0.071 mmol) in toluene were added (S)-4-ethyl-4-hydroxy-1,8-dihydro-1H-pyrano[3,4-f]indolizine-3,6,10(4H)-trione (13 mg, 0.05 mmol) and toluene-p-sulfonic acid (2 mg), and N$_2$ was then introduced. The reaction solution was refluxed under N$_2$ for 3 h, and concentrated under vacuum to remove the solvent. The resulting residue was purified by HPLC to obtain the title compound (6 mg, 30%). $^1$H NMR (DMSO-d$_6$): δ 7.92 (1H, d, J=12.4 Hz), 7.61 (1H, d, J=9.2 Hz), 7.24 (1H, s), 6.51 (1H, s), 5.41 (2H, s), 5.21 (2H, s), 4.03 (3H, s), 2.74 (3H, s), 1.87-1.83 (2H, m), 0.88-0.84 (3H, m).

Biological Activity Experiments in Vitro

The human lung cancer A549 cells were cultured in DMEM medium (Gibco®) supplemented with 10% fetal bovine serum (Hyclone®), and human colon cancer SW620, HT-29 cells and human prostate cancer PC-3 cells were cultured in RPMI-1640 medium (Gibco®) supplemented with 10% fetal bovine serum (Hyclone®). The cells described above were cultured in 25 cm$^2$ or 75 cm$^2$ plastic cell culture flask (Corning®) filled with 95% air and 5% CO$_2$ at 37° C., for 2~3 passages per week.

Cells were seeded in 96 well cell culture plates (Corning®) at a density of 1×10$^3$ cells/well (A549), 2×10$^3$ cells/well (SW620 and HT-29), 3×10$^3$ cells/well (PC-3), 195 μL/well, and cultured at 37° C., under 95% air and 5% CO$_2$. After 24 h, compounds of this disclosure were added. All the compounds (dissolved in 100% DMSO) were serially diluted three times by 100% DMSO starting from 10 mM. 4 μL of the solution of each concentration was added to 96 μL serum free medium, respectively, and 5 μL diluted solution by medium was added to the culture plates seeded with the cancer cells. The final concentration of DMSO in culture medium was 0.1%, and the final concentration of the compound was 0.3 nM~10 μM. The said cells were incubated at 37° C. for 3 days.

3 Days later, the viabilities of viable cells were measured by luminescent plate reader according to the reaction of ATP and luciferase (Cell Titre Glo® Luminescent Cell Viability Assay, Promega). This method can be used to evaluate effectiveness of the compounds according to their influences on the cell growth. The dose response curves were generated by the obtained data, and IC$_{50}$ values were calculated with the program Prism.

Biological activities of the compounds of this disclosure:

| Compounds | A549 IC$_{50}$ (nM) | HT-29 IC$_{50}$ (nM) | PC-3 IC$_{50}$ (nM) | SW620 IC$_{50}$ (nM) |
|---|---|---|---|---|
| Example 1 | <100 | <100 | <500 | <100 |
| Example 2 | >1000 | <1000 | >1000 | <500 |
| Example 3 | <500 | <1000 | >1000 | <500 |
| Example 4 | <100 | >1000 | <500 | <100 |
| Example 5 | <100 | <500 | <500 | <100 |
| Example 6 | >1000 | <1000 | >1000 | <500 |
| Example 7 | <100 | <100 | <100 | <100 |
| Example 8 | <100 | <100 | <100 | <100 |
| Example 9 | <100 | <100 | <100 | <100 |
| Example 10 | <500 | <500 | <500 | <100 |
| Example 11 | <100 | <500 | <100 | <100 |
| Example 12 | <100 | <100 | <100 | <100 |

While preferred embodiments of the present disclosure have been shown and described herein, such embodiments are provided as examples only. It should be understood that various alternatives to the embodiments of the disclosure described herein may be employed in practicing the disclosure. Those ordinary skilled in the art will appreciate that numerous variations, changes, and substitutions are possible without departing from the disclosure. It is intended that the appended claims define the scope of aspects of the disclosure and that methods and structures within the scope of these claims and their equivalents are covered thereby.

The invention claimed is:
1. A compound selected from the group consisting of:

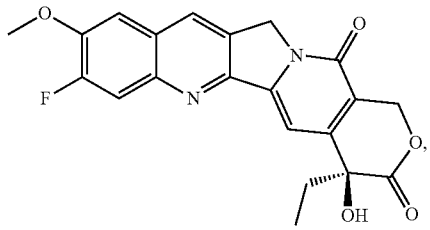

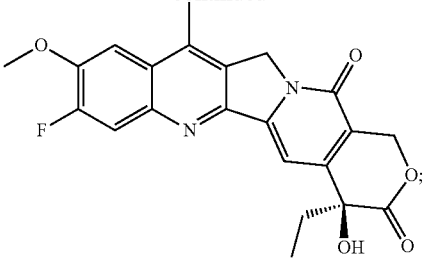

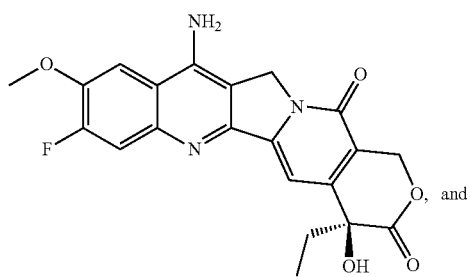

or a pharmaceutically acceptable salt thereof.

2. A pharmaceutical composition comprising the compound according to claim 1, or a pharmaceutically acceptable salt thereof, and a pharmaceutically acceptable carrier.

3. A method for treating a tumor in a mammal in need thereof, comprising administering to the mammal a therapeutically effective amount of the compound of claim 1, or a pharmaceutically acceptable salt thereof, or the pharmaceutical composition of claim 2, wherein the tumor is selected from the group consisting of lung cancer, colon cancer and prostate cancer.

4. The method of claim 3, wherein the mammal is a human being.

* * * * *